(12) United States Patent
Ling

(10) Patent No.: US 12,415,009 B2
(45) Date of Patent: Sep. 16, 2025

(54) SYSTEMS AND METHODS FOR AIR TREATMENT USING UV IRRADIATION

(71) Applicant: Feng Ling, East Brunswick, NJ (US)

(72) Inventor: Feng Ling, East Brunswick, NJ (US)

( * ) Notice: Subject to any disclaimer, the term of this patent is extended or adjusted under 35 U.S.C. 154(b) by 1055 days.

(21) Appl. No.: 17/396,416

(22) Filed: Aug. 6, 2021

(65) Prior Publication Data
US 2022/0040363 A1  Feb. 10, 2022

Related U.S. Application Data

(60) Provisional application No. 63/063,076, filed on Aug. 7, 2020.

(51) Int. Cl.
*A61L 9/20* (2006.01)

(52) U.S. Cl.
CPC ............. *A61L 9/20* (2013.01); *A61L 2209/12* (2013.01); *A61L 2209/15* (2013.01)

(58) Field of Classification Search
CPC ........ A61L 9/20; A61L 9/205; A61L 2209/12; A61L 2209/15
See application file for complete search history.

(56) References Cited

U.S. PATENT DOCUMENTS

| | | |
|---|---|---|
| 6,893,610 B1 | 5/2005 | Barnes |
| 2009/0041632 A1 | 2/2009 | Day et al. |
| 2013/0291735 A1 | 11/2013 | Livchak et al. |
| 2015/0136671 A1 | 5/2015 | Barnes |
| 2018/0264160 A1 | 9/2018 | Benedek et al. |
| 2018/0271080 A1 | 9/2018 | Kim et al. |
| 2021/0283285 A1* | 9/2021 | Li ............................ A61L 9/20 |

FOREIGN PATENT DOCUMENTS

WO  WO-2010087831 A1 *  8/2010 ............... A61L 2/10

OTHER PUBLICATIONS

Theia Group, LLC, International Search Report and Written Opinion, PCT Application No. PCT/US21/45063, Nov. 17, 2021, 12 pages.
Jun-Won Kang, et al., "The Synergistic Bactericidal Mechanism of Simultaneous Treatment with a 222-Nanometer Krypton-Chlorine Excilamp and a 245-Nanometer Low-Pressure Mercury Lamp," Applied and Environmental Microbiology, American Society for Microbiology, vol. 85 Issue 1 e01952-18, pp. 1-14, Jan. 2019, 14 pages.

* cited by examiner

*Primary Examiner* — Timothy C Cleveland
(74) *Attorney, Agent, or Firm* — USCH Law, PC

(57) ABSTRACT

An air treatment system includes an enclosure, a first UV lamp, a second UV lamp, and one or more air driving components. The enclosure includes an inlet, an outlet, and a passageway between the inlet and the outlet. The one or more air driving components are configured to draw air into the enclosure via the inlet, and to direct air toward the outlet via the passageway. The first UV lamp is configured to output first UV light having a first peak wavelength, and the second UV lamp is configured to output second UV light having a second peak wavelength that is different from the first peak wavelength. The first and second UV lamps are disposed in the enclosure, and each of the first light and the second light irradiates the passageway. A method of operating the air treatment system is also disclosed.

19 Claims, 18 Drawing Sheets

SYSTEMS AND METHODS FOR AIR TREATMENT USING UV IRRADIATION

CROSS REFERENCE TO RELATED APPLICATIONS

The present application is a non-provisional application of U.S. Provisional Application No. 63/063,076, filed Aug. 7, 2020, entitled "Systems and Methods for Air Treatment Using US Irradiation," which is incorporated by reference herein in its entirety.

TECHNICAL FIELD

This application relates generally to air decontamination, and more particularly, to systems and methods for air treatment using UV irradiation.

BACKGROUND

Airborne pathogens can make indoor gatherings unsafe, as recently demonstrated by the COVID-19 pandemic. While many indoor gatherings can be avoided, certain activities still require people to congregate indoors or in enclosed spaces. For example, people may still need to use public transportation, seek medical care, or perform essential activities indoors, such as hospitals, nursing homes, buses, trains, airplanes, airports, grocery stores, etc. Therefore, there is a great need for effective decontamination of airborne or aerosolized pathogens.

While ultraviolet (UV) light has been effectively used to decontaminate surfaces due to its proven germicidal capabilities, using UV light to sterilize air faces several challenges. First of all, UV radiation can be hazardous so it should not be used to irradiate spaces where people and animals are present. Secondly, using commercial UV lamps to eliminate air-borne pathogens normally requires a minimum treatment time of at least 15 minutes. As a result, UV light has mainly been used to decontaminate unoccupied spaces (e.g., a hospital room between patients or office spaces or shopping malls after business hours). Such systems are not suitable for preventing airborne diseases, such as tuberculosis or pandemic influenza, which are usually transmitted via airborne droplets carrying pathogens while people are in close proximity to one another.

SUMMARY

Therefore, it is imperative to develop effective systems and methods of air decontamination.

The disclosed embodiments provide an air treatment system that can operate continuously to decontaminate (e.g., disinfect, sterilize) air in an enclosed space (e.g., a room, passenger vehicle, etc.) whether or not the space is occupied. The air treatment system circulates air through an enclosure irradiated with UV light of at least two distinct peak wavelengths from at least two sets of UV lamps. The air treatment system is highly effective in deactivating (e.g., killing, destroying or neutralizing) airborne pathogens such as bacteria, spores, and viruses in the air flowing through the enclosure before it is released into the ambient, due largely to the synergistic effect from the combined wavelengths results In some embodiments, the multiple types of UV lamps include one or more first UV lamps configured to emit first UV light having first peak wavelength (e.g., 254 nm) and one or more second UV lamps configured to emit second UV light having a second peak wavelength (e.g., 195 nm, 207 nm, 222 nm or 232 nm) that is different from the first peak wavelength. The one or more first UV lamps can include, for example, one or more mercury vapor lamps and/or one or more UV Light Emitting Diodes (UV LED) configured to emit UV light near the first peak wavelength. The one or more second UV lamps can include, for example, one or more excilamps and/or one or more UV LED's configured to emit UV light near the second peak wavelength. In some embodiments, the first peak wavelength is longer than the second peak wavelength by at least 20 nm. In some embodiments, the first peak wavelength is very close to the wavelength for maximum DNA absorption, so it is very effective at destroying the RNA/DNA of a pathogen. The second UV light, with the shorter peak wavelength, such as 222 nm UV, can inflict damages to RNA/DNA, protein, lipid/cell membrane, and enzymes simultaneously. By including both the first UV lamp(s) and the second UV lamp(s), the air treating system according to some embodiments (e.g., system 100, 200, 202, 204, 206, 208, or 210) makes use of the synergetic effect of the combined wavelengths to deactivate pathogens, and achieves a much faster deactivation rate than systems that use single-wavelength UV light. In other words, by irradiating the air flowing through the enclosure with light of at least two distinct UV wavelengths that are, for example, more than 20 nm apart, a minimum treatment time to decontaminate the air by, for example, deactivating at least 90% or 99% of the active pathogens in the air, is significantly reduced. For example, by exposing the air to UV light of two distinct wavelengths (e.g., 222 nm and 254 nm), the air may be decontaminated within a time frame of 0.01-2 seconds, which is drastically shorter than the minimum treatment time of 15 minutes or more using UV light of 254 nm peak wavelength. This enables the air treatment system to decontaminate the air in a 12 ft×12 ft room in less than 2 minutes, making the indoor space almost as safe as outdoor space.

In accordance with some embodiments, the air treatment system includes an enclosure (e.g., a flow-through enclosure), one or more first UV lamps, one or more second UV lamp, and one or more air driving components. The enclosure includes an inlet, an outlet, and a passageway (e.g., air passageway) between the inlet and the outlet. The one or more air driving components are configured to draw air into the enclosure and to direct the air toward the outlet of the enclosure via the passageway. The one or more first UV lamps are disposed in the enclosure and is configured to irradiate the passageway with first light having a first peak wavelength (e.g., the first light has a normalized spectrum that peaks at the first peak wavelength). The one or more second UV lamps are disposed in the enclosure and is configured to irradiate the passageway with second light having a second peak wavelength that is distinct from the first peak wavelength (e.g., the second light has a normalized spectrum that peaks at the second peak wavelength).

In accordance with some embodiments, a method of air treatment includes drawing air into an enclosure via an inlet, and directing the air toward an outlet of the enclosure via a passageway that is concurrently irradiated by at least one first UV lamp and at least one second UV lamp disposed in the enclosure, the at least one first UV lamp irradiating the passageway with first light having a first peak wavelength, the at least one second UV lamp irradiating the passageway with second light having a second peak wavelength that is distinct from the first peak wavelength. Each of the one or more second UV lamps are distinct from each of the one or more first UV lamps. The method further includes outputting air from the outlet of the enclosure after the air has received a combined radiation dosage of the first light and the second light that is less than 1.2 mJ/cm$^2$ or even less than 0.6 mJ/cm$^2$.

BRIEF DESCRIPTION OF THE DRAWINGS

For a better understanding of the various described embodiments, reference should be made to the Detailed Description below, in conjunction with the following drawings in which like reference numerals refer to corresponding parts throughout the Figures.

DETAILED DESCRIPTION

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

Many modifications and variations of this disclosure can be made without departing from its spirit and scope, as will be apparent to those skilled in the art. The specific embodiments described herein are offered by way of example only, and the disclosure is to be limited only by the terms of the appended claims, along with the full scope of equivalents to which such claims are entitled.

Figure 1A:
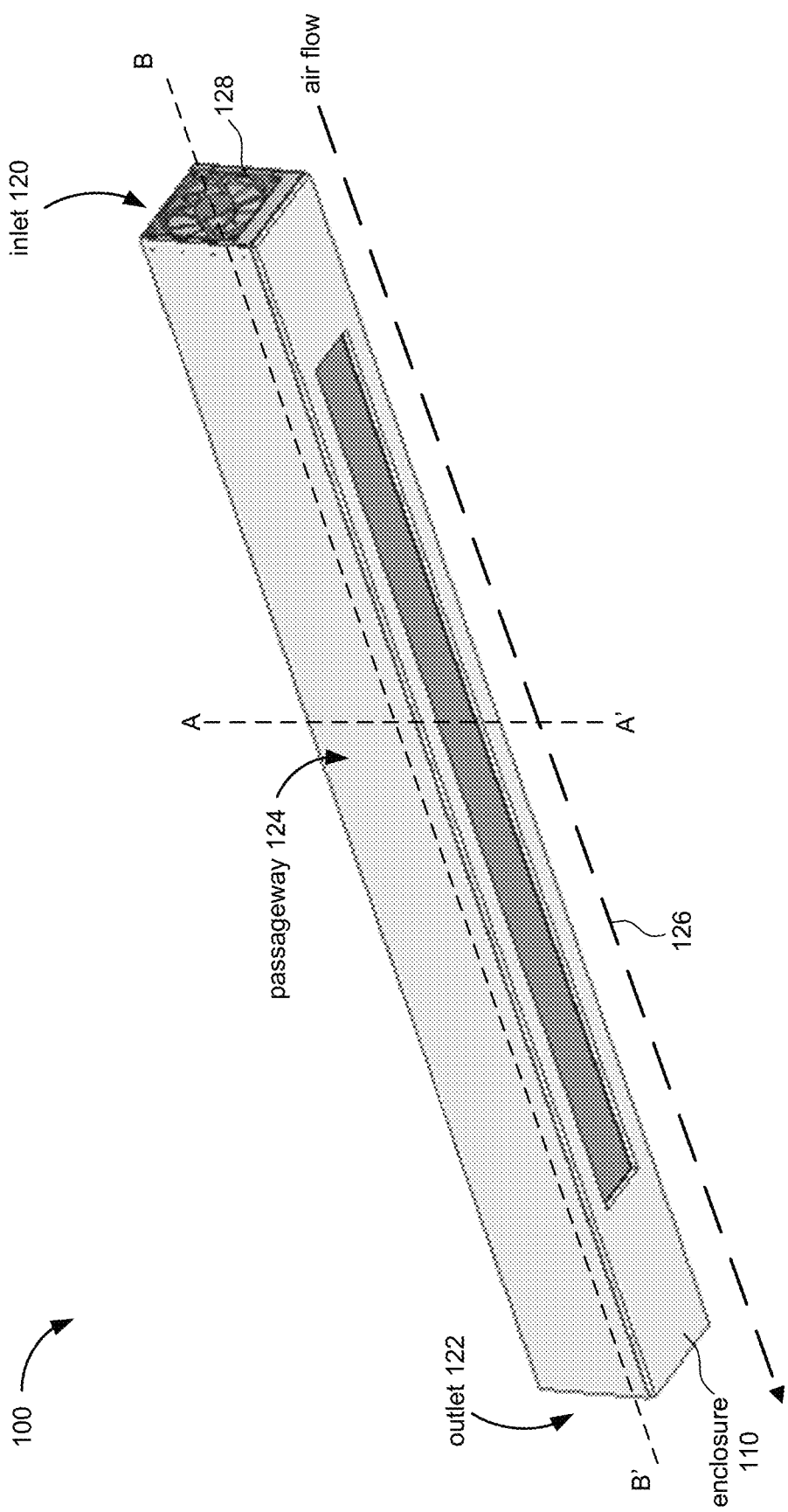
FIG. 1A illustrates an air treatment system in accordance with some embodiments.
Figure 1B:
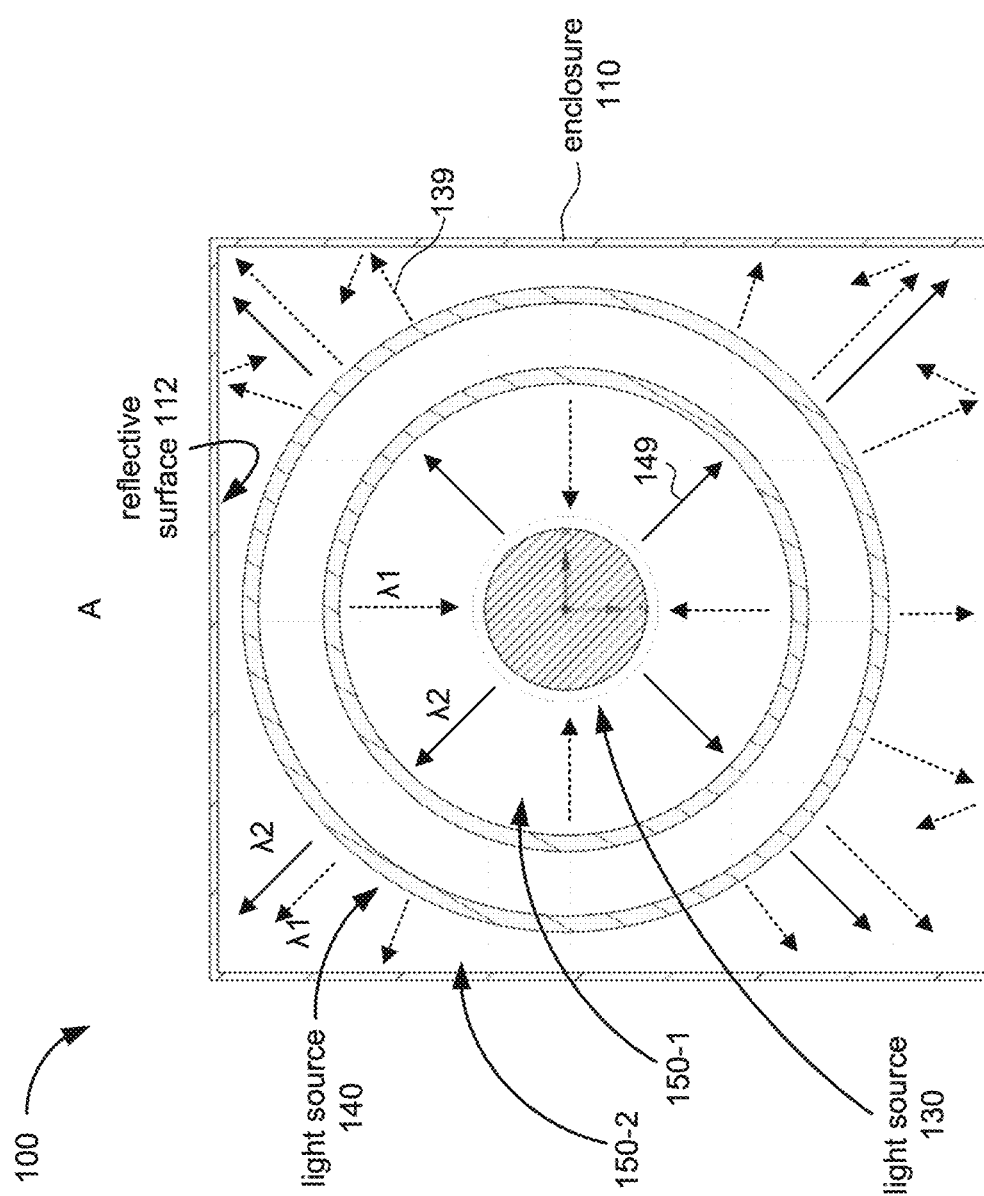
FIG. 1B illustrates a cross-sectional view of the air treatment system shown in FIG. 1A in accordance with some embodiments.
Figure 1C:
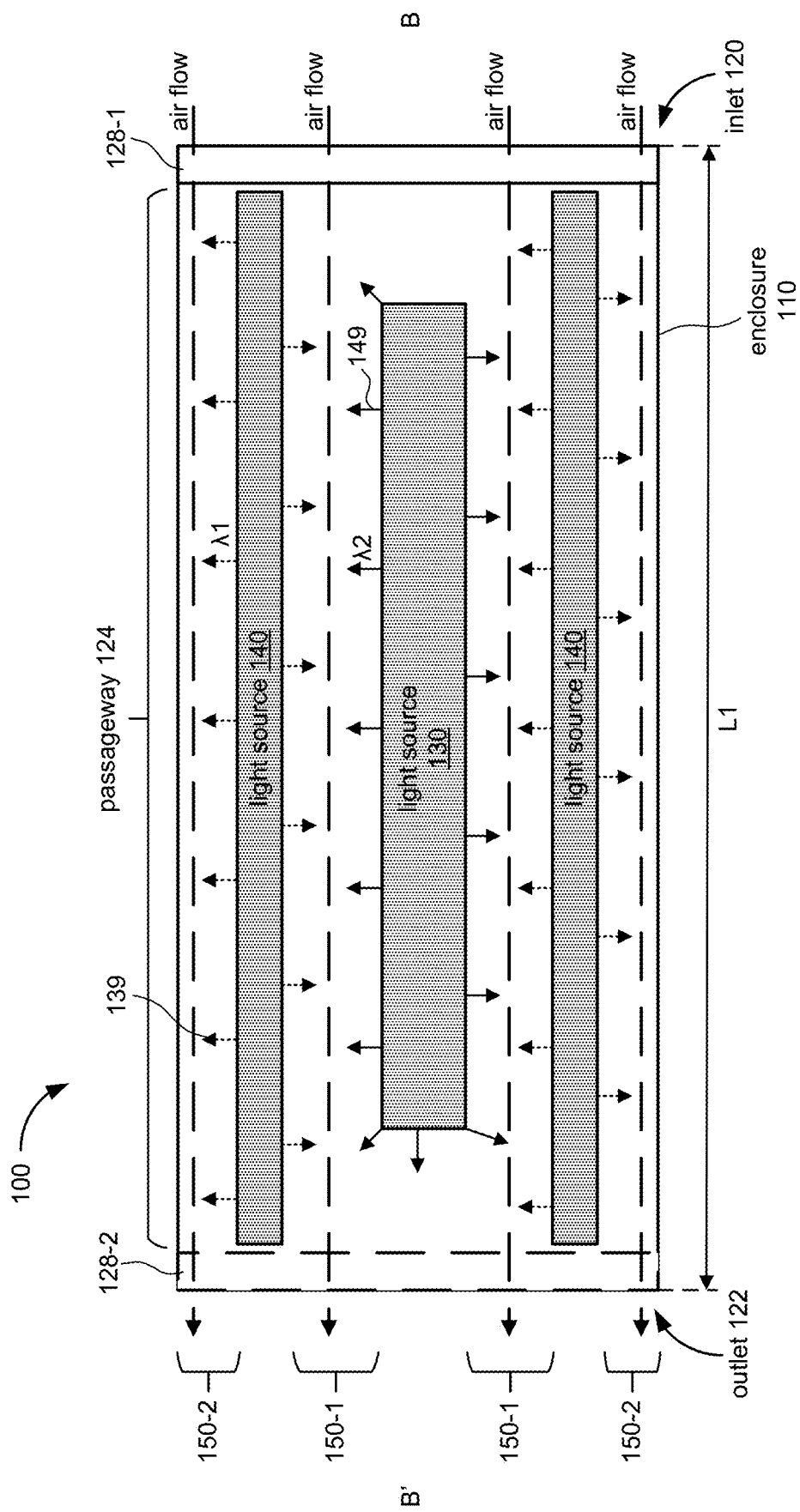
FIG. 1C-1D illustrates cross-sectional views of the air treatment system shown in FIG. 1A in accordance with some embodiments.

FIGS. 1A-1C illustrates an air treatment system 100 in accordance with some embodiments. The air treatment system includes an enclosure 110. The enclosure has an inlet 120, an outlet 122, and a passageway 124 disposed between the inlet 120 and the outlet 122. The enclosure 110 also includes one or more air driving components 128 (e.g., a fan) that is configured to draw air into the enclosure 110 through the inlet 120, direct air via the passageway 124 in the enclosure 110 toward the outlet 122, wherein the air is driven out of the enclosure 110. Arrow 126 illustrates a general direction of air flow through the enclosure 110 of the air treatment system 100. The air treatment system 100 is configured to decontaminate air by deactivating airborne pathogens in the air that flows through the air treatment system 100. For example, the number of active pathogens (such as bacteria, mold spores, or viruses) that are present in air that enters the enclosure 110 are reduced as the air flows through the enclosure 110. The air treatment system 100 provides optical decontamination (e.g., disinfection, sterilization) of air by irradiating the air using different types of UV lamps.

In some embodiments, the air treatment system 100 can be installed or disposed in an indoor or enclosed space (such as a room, an office, a hospital, or a shopping mall, etc.), and works to circulate air within the space through the enclosure so that the air can be decontaminated by UV light from the different types of UV lamps.

A cross-sectional view along the AA' direction of the air treatment system 100 is shown in FIG. 1B. The air treatment system 100 includes one or more UV lamps 130 that are configured to output first light 139 having a first peak wavelength ($\lambda$1), and one or more UV lamps 140 that are configured to output second light 149 having a second peak wavelength ($\lambda$2). The UV lamps 130 and 140 are disposed in the enclosure 110 such that the first light 139 and the second light 149 irradiate the passageway 124. The UV lamps 130 and 140 output ultraviolet (UV) light (e.g., light having wavelengths in the UV portion of the spectrum of electromagnetic waves).

In some embodiments, the difference between the first peak wavelength ($\lambda$1) and the second peak wavelength ($\lambda$2) is greater than 20 nm. For example, the first peak wavelength may be 254 nm and the second peak wavelength may be 195 nm, 207 nm, 222 nm or 232 nm, or vice versa.

In some embodiments, the first peak wavelength and the second peak wavelength may be a wavelength in any of the ultraviolet-A (UV-A) band (e.g., between 320 nm to 400 nm), the ultraviolet-B (UV-B) band (e.g., between 290 nm to 320 nm), or the ultraviolet-C (UV-C) band (e.g., 100 nm to 290 nm), or vice versa. In some embodiments, each of the first peak wavelength ($\lambda$1) and the second peak wavelength ($\lambda$2) is between 300 nm and 195 nm.

In some embodiments, UV lamp(s) 130 include a first type of UV lamp and the UV lamp(s) 140 include a second type of UV lamp that is different from the first type. For example, UV lamp(s) 130 may include a mercury-vapor lamp that emits light with a peak wavelength at 254 nm, and UV lamp 140 may include an excimer lamp (e.g., excilamp) that produces UV light from an excited molecule complex (e.g., an exciplex) between two electrodes spaced apart by about 5-10 mm. In some embodiments, UV lamp(s) 140 includes a Krypton-Chlorine lamp that emits light with a peak wavelength of 222 nm and/or a Krypton-Bromine lamp that that emits light with a peak wavelength of 207 nm. In some embodiments, either or both of the first UV lamp(s) 130) and the second UV lamp(s) 140 can include UV Light Emitting Diodes (UV LED). For example, the one or more second UV lamps can include one or more UV LED's configured to emit UV light with a peak wavelength of 232 nm.

In some embodiments, as shown in FIG. 1B, UV lamp(s) 130 and UV lamp(s) 140 are arranged concentrically with respect to each other and at least one of the UV lamp(s) 130 and UV lamp(s) 140 divides the passage way into multiple chambers, such as an inner chamber 150-1 surrounding a UV lamp 130 and surrounded by a UV lamp 140, and an outer chamber 150-2 surrounding the inner chamber 150-1 and separated from the inner chamber by the UV lamp 140. In some embodiments, UV lamp(s) 130 and UV lamp(s) 140 are arranged concentrically with respect to each other and with respect to a central axis 160 of the passageway. For example, as shown in FIG. 1B, UV lamp(s) 130-1 includes a mercury vapor lamp disposed along the center axis of the passageway, while UV lamp(s) 140 includes an excilamp disposed around the center axis of the passageway. In some embodiments, the excilamp includes one or more types of exciplex in a sealed space within a casing made of a material (e.g., quartz) that is transparent to UV light in the range of 190 nm to 300 nm so both the first light and the second light can pass through the excilamp and irradiate both the inner chamber 150-1 and the outer chamber 150-2. In some embodiments, the casing providing the sealed space for the exciplex(es) includes two concentric walls that are spaced about 8 mm-10 mm from each other, and the excilamp further includes conductive meshes disposed along the two concentric walls as electrodes. In some embodiments, an inside surface 112 of the enclosure 110 is a reflective surface that is configured to reflect the first light 139 and the second light 149 incident upon the surface 112 to make sure that an entirety or nearly the entirety (e.g., 90%) of the passageway is irradiated by both the first light and the second light. A highly reflective surface on the inside of the enclosure 110 also increases the amount of light in the passageway 124 compared to an enclosure 110 that does not include a reflective inner surface.

The passageway 124 has a length, L1, such that air flowing through the passageway 124 travels a distance that is at least equal to the length, L1 before being released through the outlet. In some embodiments, at least one chamber of the one or more chambers 150 has the same length as the passageway 124 (e.g., at least one chamber has a length that is equal to L1). In some embodiments, at least one chamber of the one or more chambers 150 has a length that is shorter than the passageway 124 (e.g., at least one chamber has a length that is shorter than L1). In some embodiments, all of the chambers 150 have a same length. In some embodiments, a chamber of the one or more chambers 150 has a length that is different from another chamber of the one or more chambers 150. In some embodiments, the length, L1, of the passageway 124 is at least 400 mm.

In some embodiments, more than 90% of the pathogens in the air flowing through the passageway would be irradiated by both the first light and the second light, and can be deactivated after receiving a combined radiation dosage of less than 1.2 mJ/cm$^2$. In some instances, the pathogens can be deactivated after receiving a combined radiation dosage of even less than 0.6 mJ/cm2. In some embodiments, the first light or the second light contributes 5-95% of the combined dosage. In some embodiments, the first light or the second light contributes 10-90% of the combined dosage. For example, air flowing through the passageway 124 is irradiated by each of the first light 139 and the second light 149 for at least 90% of its travel time (e.g., travel duration) in the passageway 124 (or in a chamber 150 of the passageway 124). In another example, air flowing through the chamber 150-1 of the passageway 124 is irradiated by each of the first light 139 and the second light 149 for at least 90% its travel time (e.g., travel duration) in the passageway 124 (or in a chamber 150 of the passageway 124), and air flowing through the chamber 150-2 of the passageway 124 is irradiated by the second light 149 for at least 90% of its travel time (e.g., travel duration) in the passageway 124 (or in a chamber 150 of the passageway 124).

In some embodiments, air flowing through passageway 124 may be exposed to the first light 139 for a first time duration, T1 and the air flowing through passageway 124 may be exposed to the second light 149 for a second time duration, T2. In some embodiments, at least one of the first time duration, T1, and the second time duration, T2, is at least 90% of a total time duration that it takes for the air to flow through the passageway 124. In some embodiments, a time duration T0 in which the air is exposed to both the first light 139 and the second light 149 is at least 90% of any of the first time duration, T1, and the second time duration, T2.

A second cross-sectional view along the BB' direction of the air treatment system 100 is shown in FIG. 1C. As shown, in some embodiments, the UV lamp 130 (e.g., a mercury vapor tube) is surrounded by and is concentric with the UV lamp 140 (e.g., an excilamp). As shown, the passageway 124 is divided into 2 chambers 150-1, 150-2 by UV lamp 140. In some embodiments, UV lamps 130 and 140 are arranged such that air flowing through chamber 150-1 would receive a first combined radiation dosage that is about the same as a second combined radiation dosage as air flowing through chamber 150-2, although the percentage of either the first light or the second light contributing to the first combined dosage may be slightly or somewhat different as compared to the percentage of either the first light or the second light contributing to the second combined dosage. In some embodiments, as shown in FIG. 1C, the first UV lamp 130 may have a shorter length along the passageway than the second UV lamp 140 so that less of the first light 139, which can be harmful to humans and animals, can escape the enclosure 110 via the inlet and/or the outlet. Any difference in lengths of the first and second UV lamps may also be due to manufacturing requirements. In some embodiments, the first UV lamp 130 may have about the same length along the passageway as the second UV lamp 140, and shielding mechanisms can be placed at the inlet and/or the outlet to prevent anyone near the air treatment system 100 from being exposed to any UV light escaping the enclosure via the inlet and/or the outlet. In some embodiments, replaceable air filters can be placed at the inlet and/or the outlet. The air filters can be designed to block dust or other large air pollution particles from entering and/or existing the enclosure, while at the same time blocking UV light from escaping the enclosure through the inlet and/or the outlet.

In some embodiments, as shown in FIG. 1A, the one or more air driving components 128 includes a first air driving component 128-1 (such as a fan) that is disposed at the inlet 120 of the enclosure 110, and a second air driving component 128-2 (such as a fan) that is disposed at the outlet 122 of the enclosure 110. In some embodiments, as shown in FIG. 1C, the passageway 124 has a length, L1, such that air directed through the passageway 124 travels a distance that is at least equal to the length, L1, of the passageway 124. In some embodiments, the one or more air driving components 128 operate such that air passing through the passageway 124 takes about 0.01 seconds to about 2 seconds to traverse the passageway 124 having the length, L1. In some embodiments, the one or more air driving components 128 operate at a predetermined air flow speed or air flow rate such that the air passing through the passageway 124 takes between 0.01 seconds and 2 seconds to traverse the passageway 124 having the length, L1. In some embodiments, the one or more air driving components 128 are also configured to provide temperature control (e.g., cooling) for the UV lamps 130 and 140.

Figure 1D:
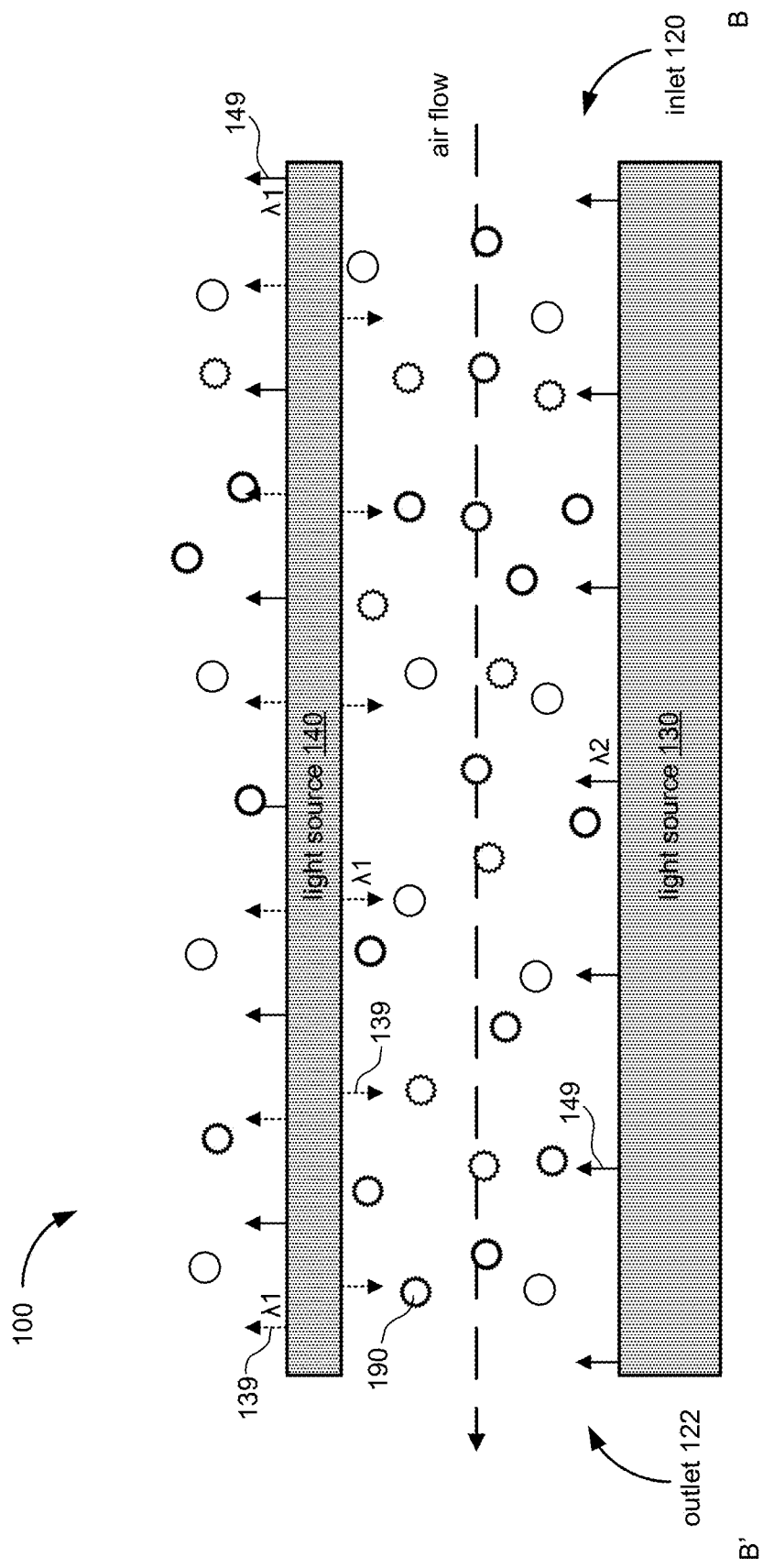

Another cross-sectional view along the BB' direction of the air treatment system 100 is shown in FIG. 1D. In this example, air passing through the air treatment system 100 includes contaminants, such as particles (e.g., dander, dust) and pathogens 190 (e.g., bacteria, viruses, mold spores). In such cases, particles and pathogens 190 that are present in air that driven through the air treatment system 100 are also irradiated by the first light 139 and the second light 149. Thus, the air treatment system 100 is able to decontaminate (e.g., sterilize, disinfect) air passing through the air treatment system 100 by killing, neutralizing, destroying, or deactivating the pathogens 190 by irradiating the pathogens 190 with both the first light and the second light 149. By irradiating the air and any pathogens in the air with both the first light 139 and the second light 149, the air can be decontaminated faster and with a higher efficacy than if the air is irradiated with only the first light 139 or the second light 149. The use of two different UV lamps that emit light having different peak wavelengths allow contaminants (such as pathogens) in the air to be neutralized or deactivated with a lower dosage of radiation. For example, 99% of active pathogens may be neutralized or destroyed after being exposed to the first light 139 and the second light 149 for a few seconds or a fraction of a second. In contrast, to achieve the same efficacy with just the first light 139 or just the second light 149 (at a same total intensity), the air would need to be exposed to the first light 139 or the second light 149 for at least a few minutes. Thus, the air treatment system 100 allows faster decontamination of indoor air without significant increase in the intensity of the first and second UV lamps or the size (e.g., length) of the passageway.

In some embodiments, a combined intensity of the first light 139 and the second light 149 is about 1 mW/cm2 to about 30 mW/cm2. In some embodiments, the first light 139 has an intensity of 50 µW/cm$^2$ to about 1 mW/cm$^2$ and the second light 149 has an intensity of 1 mW/cm$^2$ to 50 mW/cm$^2$.

Thus, the combined use (e.g., via concurrent or serial irradiation) of the first light 139 and the second light 149 for air decontamination allows a lower minimum dosage to be used to neutralize pathogens. For example, the dosage values required to deactivate the SARS virus are about 10-20 mJ/cm2 using direct UVC light at a wavelength of 254 nm under controlled lab conditions. In real-life, the virus is often hidden or shaded from direct UVC light, reducing the effectiveness of the UVC light. To compensate, researchers are applying dosages of 1,000-3,000 mJ/cm2 to ensure 99.9% deactivation. In contrast, by flowing air through an enclosed passageway irradiated by both the first light 139 and the second light 149, the air treatment system 100 can reduce the dosage required to deactivate the same SARS virus carried by aerosolized particles in the air to less than 1.2 mJ/cm$^2$. In some instances, the dosage can even be reduced to less than 0.6 mJ/cm2 to achieve the same or nearly the same result. As a result, a time duration (e.g., travel time) that it takes for the aerosolized particle to be driven through the air treatment system 100 via passageway 124 can be reduced, allowing faster decontamination of indoor air without increasing the intensity of the first light 139 and the second light 149 or the length of the passageway.

FIGS. 2A-2F illustrate various configurations of the first UV(s) lamp 130 and the second UV lamp(s) 140 in air treatment systems that correspond to the air treatment system 100 shown in FIG. 1A. Thus, descriptions provided above with respect to air treatment system 100 are not repeated for brevity.

Figure 2A:
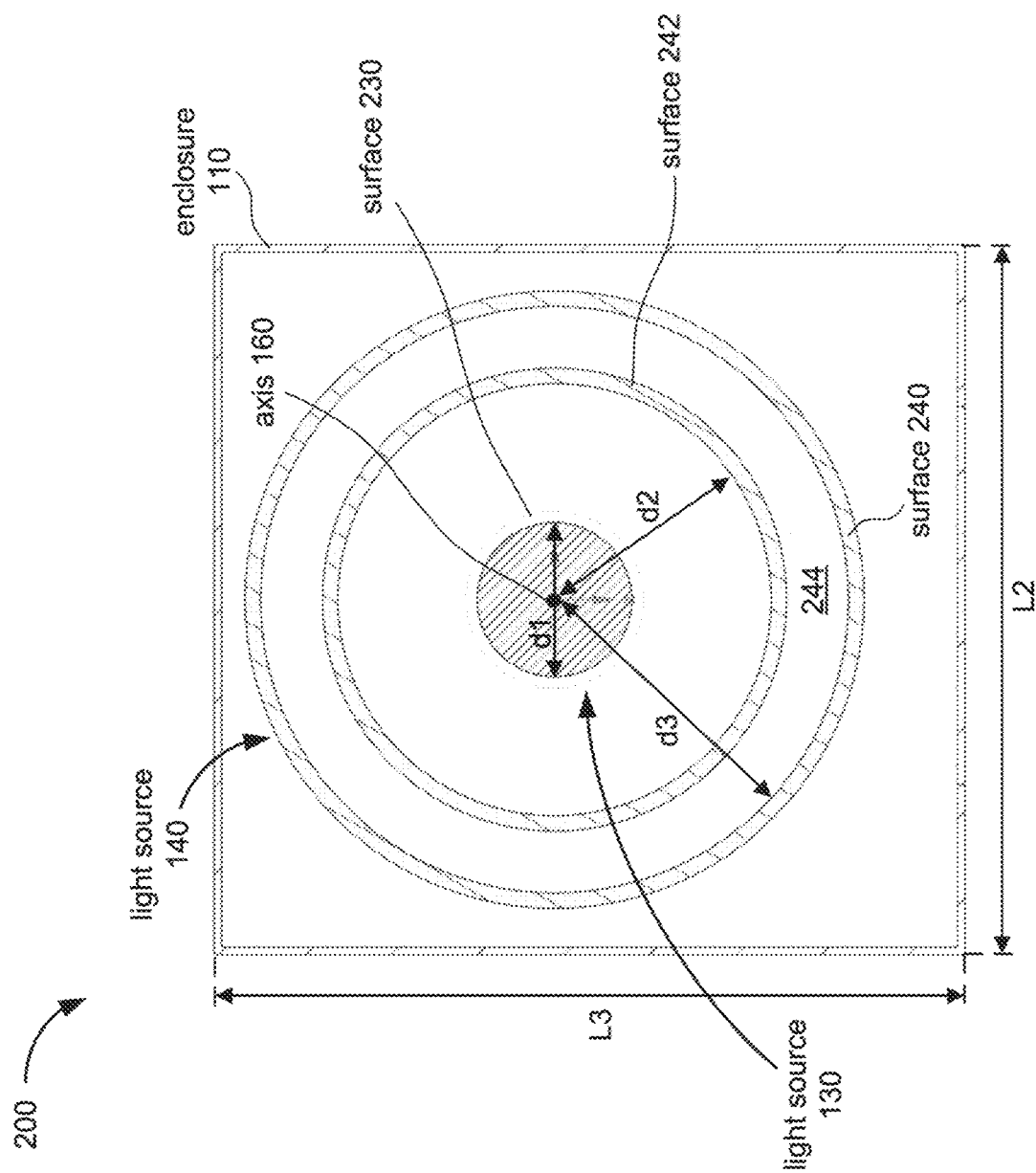
FIGS. 2A-2F illustrate different configurations of the air treatment system shown in FIG. 1A in accordance with some embodiments.

FIG. 2A shows a cross-sectional view of an air treatment system 200. In the configuration shown in FIG. 2A, the UV lamp 130 is disposed in near a central axis 160 of the enclosure 110, and the UV lamp 140 is disposed around and concentric with the UV lamp 140. In some embodiments, as shown, each of UV lamps 130 and 140 has a cylindrical shape. In this configuration, since the UV lamp 140 is surrounding the UV lamp 130, it's diameter is greater than a diameter of the UV lamp 130.

The UV lamp 130 includes a surface 230 through which the first light 139 having the first peak wavelength ($\lambda$1) is emitted into the passageway. In some embodiments, the UV lamp 130 is a mercury vapor lamp (e.g., low-pressure Mercury lamp). In some embodiments, the cross-section of the enclosure 110 may have a square or rectangular shape. For example, the enclosure may have a width, L2, that is between 60 mm to 280 mm, and a height, L3, that is between 60 mm to 280 mm. Thus, a lateral dimension (e.g., width or height) of the enclosure 110 is significantly smaller than (e.g., less than 20% of) the length, L1, of the passageway 124.

The UV lamp 140 includes surfaces 240 and 242 sandwiching (e.g., bordering two opposites sides of) a sealed space 244 (e.g., an enclosed compartment) that is occupied by one or more exciplexes. The second light 149 having the second peak wavelength ($\lambda$2) is output from the UV lamp 140 from each of the surfaces 240 and 242. In some embodiments, such as when the UV lamp 140 is an excilamp, the sealed space 244 includes one or more molecules for generating the second light 149. For example, a Krypton-Chlorine gas mixture may be disposed in the sealed space 244 so that the UV lamp 140 can generate and emit light having a peak wavelength of 222 nm. In some implementations, surfaces 240 and 242 are spaced apart by a distance that is between 7 mm and 12 mm. For example, surfaces 240 and 242 may be spaced apart by 8 mm. In another example, the surfaces 240 and 242 may be spaced apart by 10 mm. In some embodiments, each of the surfaces 240 and 242 may have a conductive mesh layer (e.g., metallic mesh layer) such that a voltage differential can be applied across the two surfaces 240 and 242. For example, surface 240 may include a first conductive mesh layer coupled to one terminal of a power source and surface 242 may include a second conductive mesh layer that is coupled to another terminal of the power source such that a voltage can be applied across the first conductive mesh layer and the second conductive mesh layer. The conductive mesh layers allow at least a portion of the light that is generated by the UV lamp 140 to be transmitted through the conductive mesh layer. In some embodiments, each of the surfaces 240 and 242 is composed of a material that is configured to transmit UV light around the second peak wavelength. For example, each of the surfaces 240 and 242 may include (e.g., be composed of) fused quartz, thereby allowing light generated by the UV lamp 130 to be emitted through surfaces 240 and 242.

Figure 2B:
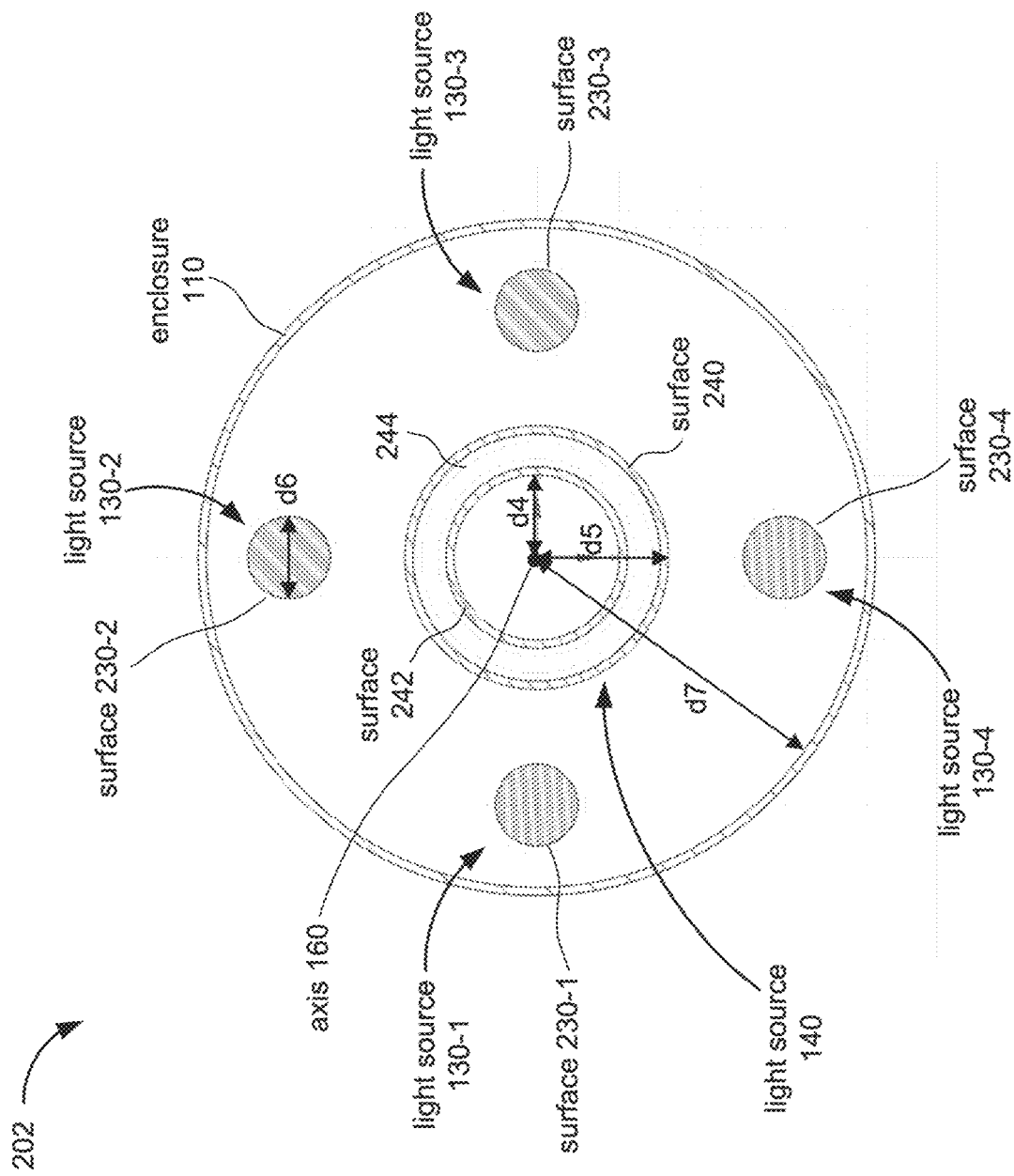

FIG. 2B shows a cross-sectional view of an air treatment system 202, showing a different concentric arrangement of the first UV lamp 130 and the second UV lamp 140. In the configuration shown in FIG. 2B, the UV lamp 140 is disposed in a central region of the enclosure 110 such that the surfaces 240 and 242 form concentric circles with respect to the central axis 160 of the enclosure 110. The air treatment system 202 also includes a plurality of UV lamps 130 (e.g., UV lamps 130-1, 130-2, 130-3, and 130-4) that are distributed along a circle that is around (or concentric with) the UV lamp 140 and/or the central axis 160 of the enclosure 110 and the UV lamp 140. The UV lamp 140 is configured to output light having the second peak wavelength ($\lambda$2) and each of the UV lamps 130 is configured to output light having the first peak wavelength ($\lambda$1). While FIG. 2B shows that there are four UV lamps 130 (e.g., UV lamps 130-1, 130-2, 130-3, and 130-4), the air treatment system 202 may include more or less UV lamps 130. For example, the air treatment system 202 may include anywhere between 3 to 8 UV lamps 130 that are distributed along one or more circles around the second UV lamp 140 and configured to output light having the first peak wavelength (λ1).

In some embodiments, surface 242 of the UV lamp 140 is a cylindrical surface that has a radius, d4, that is between 12 mm-120 mm. In some embodiments, the surface 240 of UV lamp 140 is a cylindrical surface that has a radius, d5, that is between 20 mm-140 mm. In some embodiments, surfaces 240 and 242 are concentric with one another such that surfaces 240 and 242 have a same axis of symmetry. In some embodiments, surfaces 240 and 242 are spaced apart from one another by a distance that is between 7 mm and 15 mm. For example, when surface 242 has a radius, d4, that is equal to 3 mm, surface 240 may have a radius, d5, that is equal to 7 mm.

In some embodiments, a UV lamp of the UV lamps 130 has a diameter, d6, that is between 10 mm and 38 mm. In some embodiments, each of the UV lamps 130 have a same diameter. In some embodiments, at least a UV lamp of the UV lamps 130 has a diameter that is different from another UV lamp of the UV lamps 130. For example, UV lamp 130-1 may have a radius that is different from a radius of UV lamp 130-2. Although UV lamps 130 may not be transparent to the second light 149 from UV lamp 140, the size (e.g., diameter d6) of each UV lamp 130 should be small enough to ensure that the second light 149 from UV lamp 140 can reach the area between each UV lamp 130 and the wall of the enclosure 110. For example, d6<d5, where d5 is the radius of the cylindrical outer surface 240 of the second UV lamp 140. In other words, the diameter of a UV lamp 130 can be less than half the diameter of the UV lamp 140 so as to increase the amount of second light reaching an area behind the UV lamp 130, which can be opaque to the second light 149 emitted by the UV lamps 140. In some embodiments, d6<d5/2. In some embodiments, the enclosure 110 includes a reflective inner service that also helps to direct the second light 149 to the area between each UV lamp 130 and the wall of the enclosure 110, where light emitted from the second UV source 140 cannot reach directly, to ensure that an entirety (or most of) the passageway can be sufficiently irradiated by both the first light 139 and the second light 149.

In some embodiments, the enclosure 110 may have a circular or oval shape. In some embodiments, the enclosure 110 has a lateral dimension, such as radius, d7, that is significantly smaller than (e.g., less than 20% of) a length, L1, of the passageway 124. For example, the enclosure 110 or passageway 124 may have a radius, d7, that is between 35 mm to 200 mm.

Figure 2C:
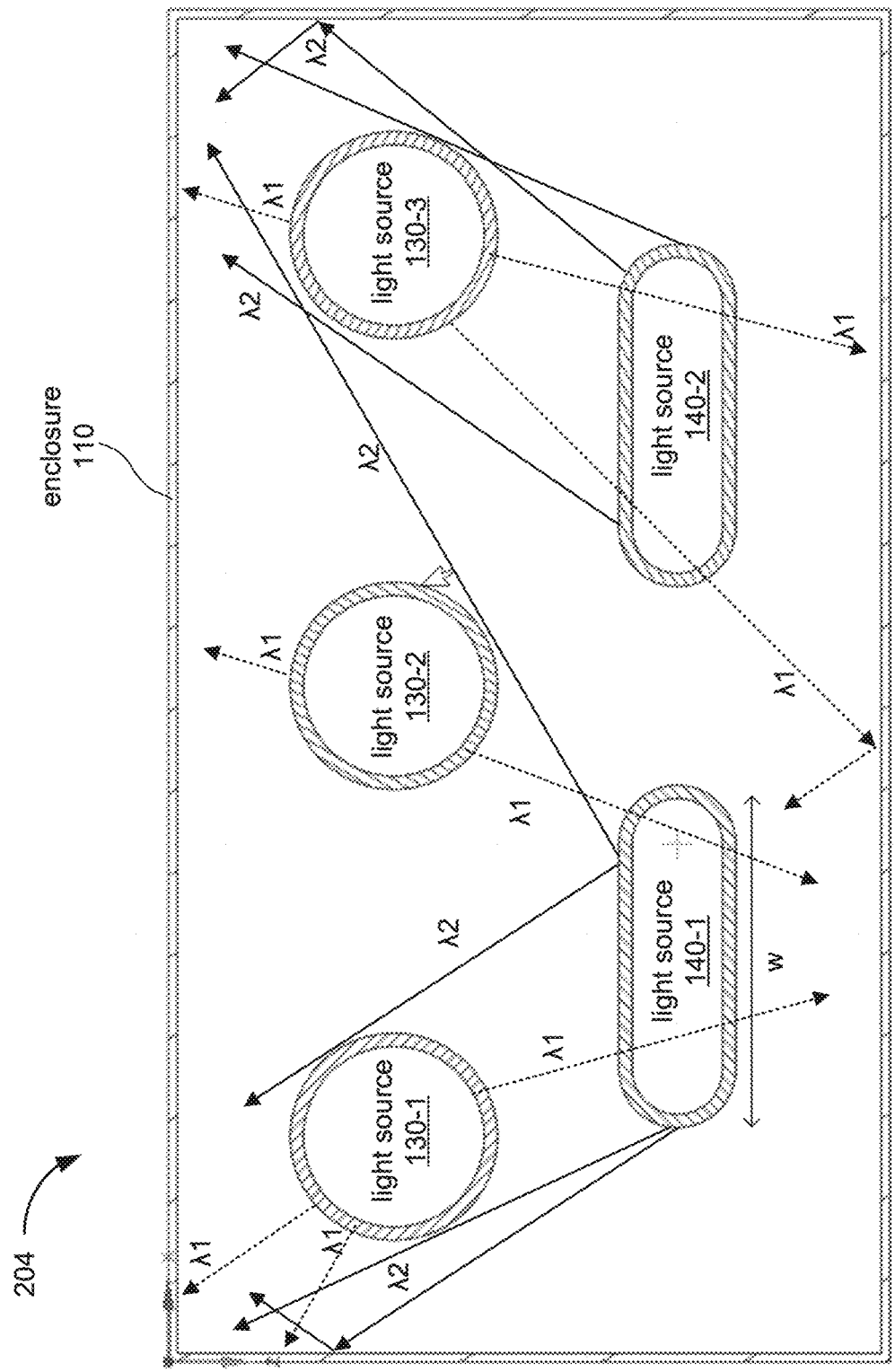

FIG. 2C shows a cross-sectional view of an air treatment system 204 that includes a plurality of UV lamps 130 (e.g., UV lamps 130-1, 130-2, and 130-3), and a plurality of UV lamps 140 (e.g., UV lamps 140-1 and 140-2), in a non-concentric arrangement. In some embodiments, as shown, the at least one of the UV lamps 140 has an oval or oblong shape (e.g., rather than a circular shape as previously shown). As shown in FIG. 2C, at least one of the UV lamps 140 can have a dimension (e.g., a width w) that is greater than a diameter of a UV lamp 130 so as to increase the amount of second light reaching an area behind each UV lamp 130, which can be opaque to the second light 149 emitted by the UV lamps 140.

Figure 2D:
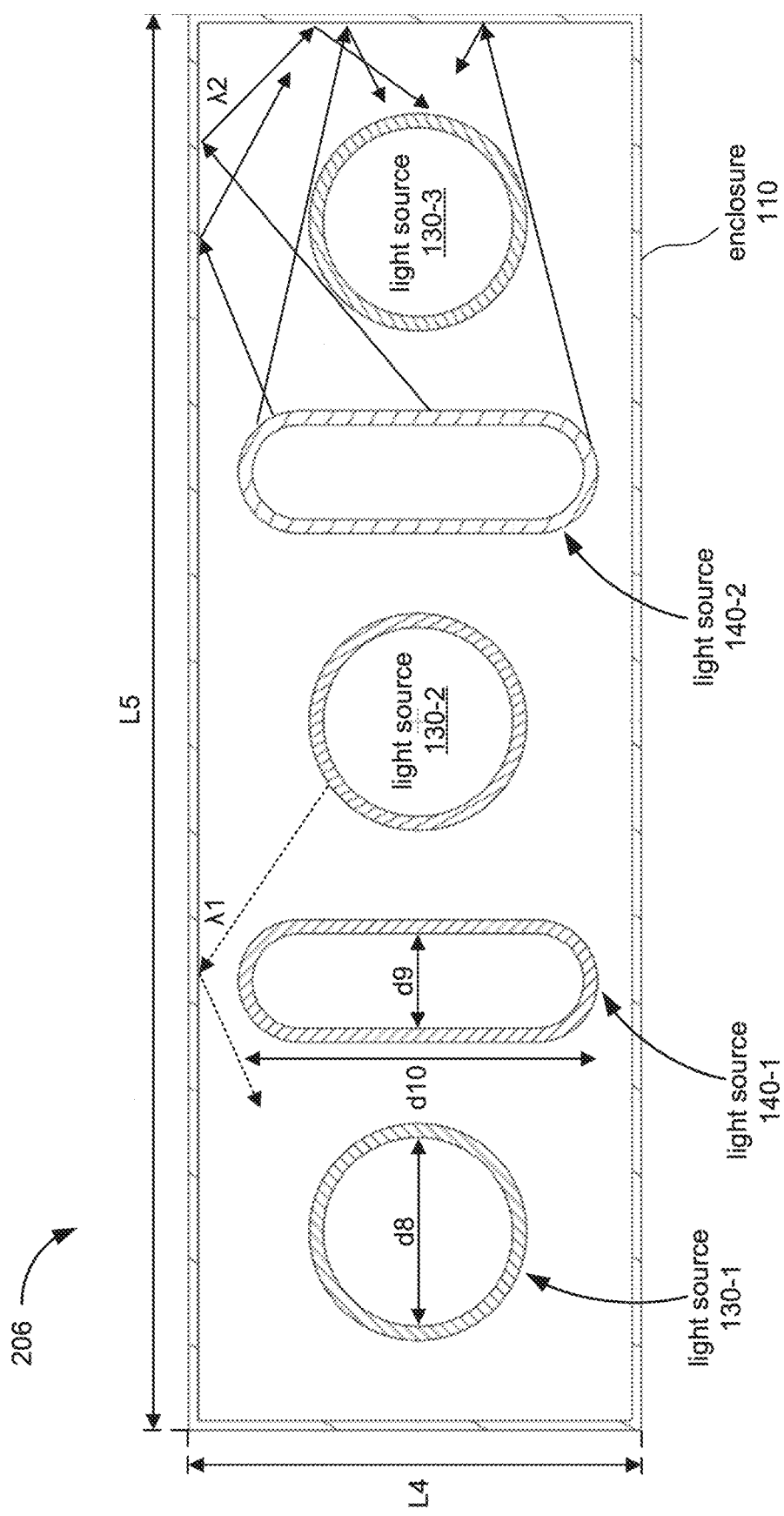

FIG. 2D shows a cross-sectional view of an air treatment system 206 that includes a plurality of UV lamps 140 (e.g., UV lamps 140-1 and 140-2), and a plurality of UV lamps 130 (e.g., UV lamps 130-1, 130-2, and 130-3) in another non-concentric arrangement.

In some embodiments, UV lamps 130-1, 130-2, and 130-3 have a diameter, d8, that is between 10 mm-38 mm. The UV lamps 130-1, 130-2, and 130-3 may have a same diameter or may have a diameter that differs from at least one other UV lamp 130.

In some embodiments, the UV lamps 140-1 and 140-2 have a width, d9, that is between 5 mm-12 mm, and a height d10 that is greater (e.g., at least twice as large as) the diameter d8 of the first UV lamp 130 to allow light from the second UV lamp 140 to reach behind the first UV lamp 130. The UV lamps 140-1, 140-2, and 140-3 may have the same sizes or different sizes. The reflective inner surface of the enclosure 110 also helps to direct the second light 149 to areas where light emitted from the UV lamps 140 cannot reach directly.

In some embodiments, the enclosure 110 may have a height, L4, that is between 60 mm-150 mm. In some embodiments, the enclosure 110 may have a width, L5, that is between 100 mm to 200 mm.

Figure 2E:
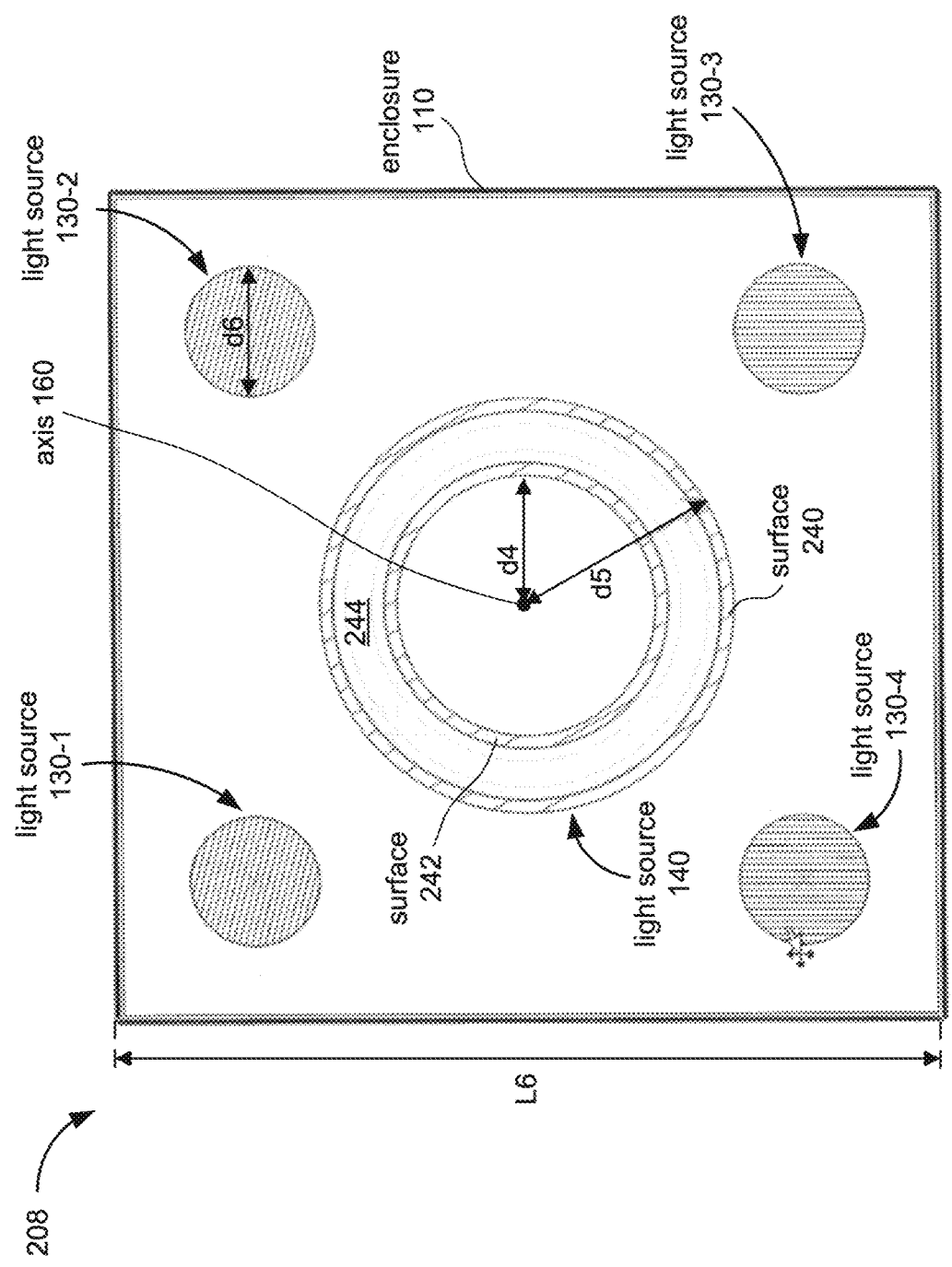

FIG. 2E shows a cross-sectional view of an air treatment system 208 that includes a UV lamp 140 that is disposed near a center axis of the enclosure 110. For example, surfaces 240 and 242 form concentric circles with respect to the central axis 160 of the enclosure 110. The air treatment system 208 also includes a plurality of UV lamps 130 (e.g., UV lamps 130-1, 130-2, 130-3, and 130-4) that are disposed around the central axis 160 of the enclosure 110 and the UV lamp 140 and near the four corners of a rectangular shaped passageway. The air treatment system 208 may include any number of UV lamps 130. For example, the air treatment system 208 may include anywhere between 3 to 8 UV lamps 130 that are configured to output light having the first peak wavelength (λ2).

In some embodiments, surface 242 of UV lamp 140 is a cylindrical surface that has a radius, d4, that is between 3 mm-120 mm. In some embodiments, the surface 240 of the UV lamp 140 is a cylindrical surface that has a radius, d5, that is between 15 mm-140 mm. In some embodiments, surfaces 240 and 242 are concentric with one another such that surfaces 240 and 242 have a same axis of symmetry. In some embodiments, surfaces 240 and 242 are spaced apart from one another by a distance that is between 7 mm and 15 mm. For example, when surface 242 has a radius, d4, that is equal to 3 mm, surface 240 may have a radius, d5, that is equal to 7 mm.

In some embodiments, a UV lamp of the UV lamps 130 has a diameter, d6, that is between 10 mm and 38 mm. In some embodiments, d6 is less than d5. In some embodiments, d6 is less than half of d5. In some embodiments, each of the UV lamps 130 have a same radius. In some embodiments, at least a UV lamp of the UV lamps 130 has a radius that is different from another UV lamp of the UV lamps 130. For example, UV lamp 130-1 may have a radius that is different from a radius of UV lamp 130-2.

Figure 2F:
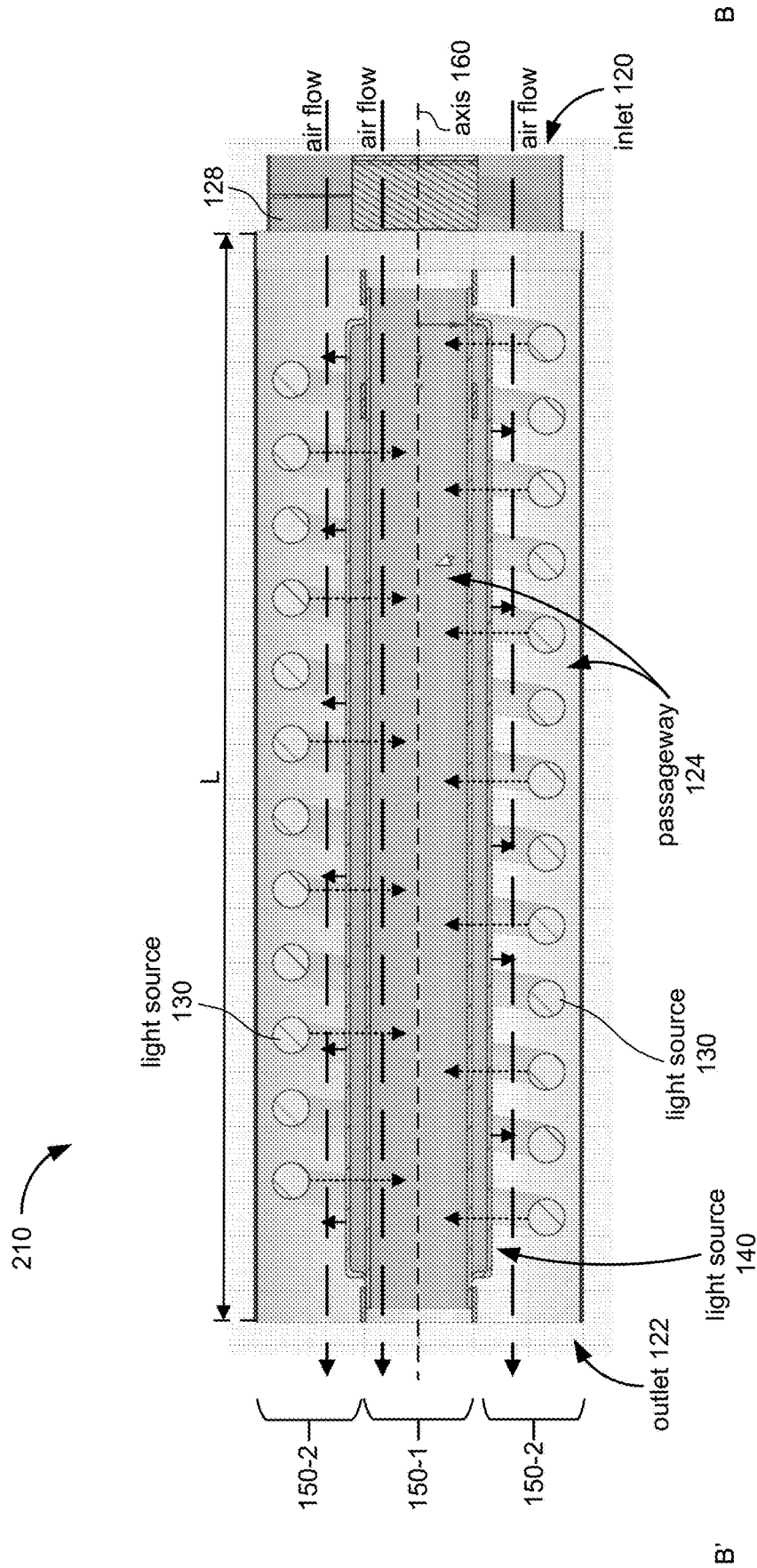

A cross-sectional view along the BB' direction of another air treatment system 210 with the first UV lamp 130 and the second UV lamp arranges concentrically with respect to each other is shown in FIG. 2F. In this example, the UV lamp 130 is a mercury vapor lamp that is coiled around the UV lamp 140, which is an excilamp having an exciplex in a sealed enclosure made of a material (e.g., quartz) that is transparent to the UV light of the first peak wavelength and the second peak wavelength. The UV lamps 130 and 140 are disposed within the enclosure 110 such that the passageway 124 can be irradiated by both the first light 139 having the first peak wavelength (λ1), represented by shot dashed arrows, and the second light 149 having the second peak wavelength (λ2), represented by solid arrows.

In some embodiments, the passageway 124 includes one or more chambers 150 (e.g., reaction chambers). FIG. 2F shows a passageway 124 that includes a first chamber 150-1 surrounded by UV lamp 140, and a second chamber 150-2 surrounding UV lamp 140 and the first chamber 150-1. Each chamber 150 allows air to flow therethrough from the inlet 120 of the enclosure 110 to the outlet 122 of the enclosure 110, and each chamber 150 receives (e.g., is irradiated by) the first light 139 having the first peak wavelength (λ1), and the second light 139 having the second peak wavelength (λ2).

In some embodiments, the enclosure 110 has a square-shaped cross-section such that a width of the enclosure 110 is the same as a height of the enclosure 110. In some embodiments, the enclosure 110 has a lateral dimension (e.g., width and/or height) that is between 40 mm to 200 mm. In some embodiments, the a lateral dimension of the enclosure 110 is at least 2, 5, or 10 times smaller than a length, L1, of the passageway 124.

An air treatment system corresponding to air treatment system 100, including any of air treatment systems 200-208, includes at least one UV lamp 130 that is configured to output first light 139 having the first peak wavelength (λ1) and at least one UV lamp 140 that is configured to output second light 149 having the second peak wavelength (λ2). The air treatment system may more than one UV lamp 140 and more than one UV lamp 130.

Figure 3:
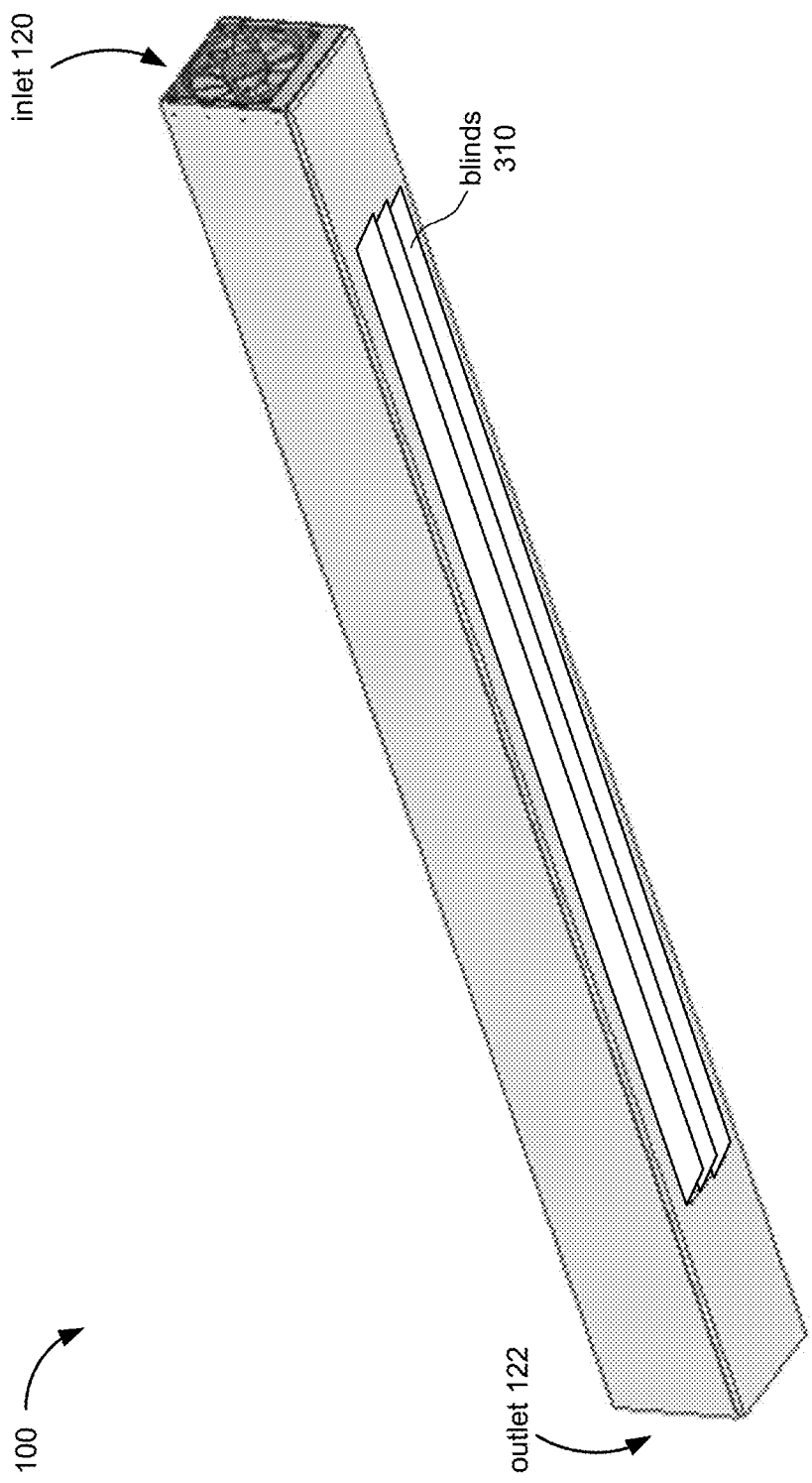
FIG. 3 illustrates an air treatment system that includes controllable blinds in accordance with some embodiments.

FIG. 3 illustrates air treatment system 100 that includes controllable blinds 310 in accordance with some embodiments. In some cases, such as when air treatment system 100 is configured for use in a room that may be occupied by humans or pets, the first and second light 139 and 149 output from UV lamps 130 and 140, respectively, are not transmitted outside the enclosure 110 when the blinds 310 are closed. In some embodiments, the blinds 310 are operable to open to allow the first light 139 and/or the second light 149 output from UV lamps 130 and 140, respectively, to irradiate surroundings outside of the enclosure 110 when the room is not occupied by people or animals.

For example, the air treatment system 100 may operate in a plurality of modes.

In a first mode, the one or more blinds 300 are in an open or partially open arrangement and the air treatment system 100 may only emit light having a wavelength that is safe for humans and pets to be exposed to. For example, if the first peak wavelength (λ1) has not been approved to be safe for direct human exposure but the second peak wavelength (λ2) has been approved as being safe for direct human exposure, while the air treatment system 100 is operating in the first mode, the UV lamp 140 may emit the second light 149 having the second peak wavelength (λ2) while the UV lamp 130 does not emit the first light 139 having the first peak wavelength (λ1). Thus, the air treatment system 100 is able to efficiently provide simultaneous air and surface decontamination while people and/or pets are in the room. A band pass filter or low pass filter can be added to the opening behind the blinds to filter out any harmful wavelengths if needed.

In a second mode, the one or more blinds 300 are in an open or partially open arrangement and the air treatment system 100 emits both the first light 139 having the first peak wavelength (λ1) and the second light 149 having the second peak wavelength (λ2) while people and pets are not present in the room. Thus, the air treatment system 100 is able to provide simultaneous air and surface decontamination that is fast and efficient.

In a third mode, the one or more blinds 300 are in a closed arrangement and the air treatment system 100 emits both the first light 139 having the first peak wavelength (λ1) and the second light 149 having the second peak wavelength (λ2). This mode can be used while people and/or pets are present in the room. Thus, the air treatment system 100 is able to efficiently provide air decontamination that is fast and has efficient.

In some embodiments, the air treatment system 100 may include or be in communication with a sensor that is able to determine whether or not humans and/or pets are present in the room. The air treatment system 100 may be able to automatically switch between the different modes based on determination, from the sensor, of whether or not people and/or pets are present in the room. For example, the air treatment system 100 may be coupled with (either wirelessly or through wired connection) a sensor (motion sensor or image sensor). In response to detection, by the sensor, that at least a person or a pet is or is likely to be in the room (or has entered the room), the air treatment system 100 would stay in the first or third mode or automatically switch from the second mode to the first mode or the third mode. In response to the sensor not detecting any person or pet in the room, the air treatment system 100 may automatically switch to the second mode to allow for fast and effective surface decontamination concurrent to air decontamination.

Figure 4:
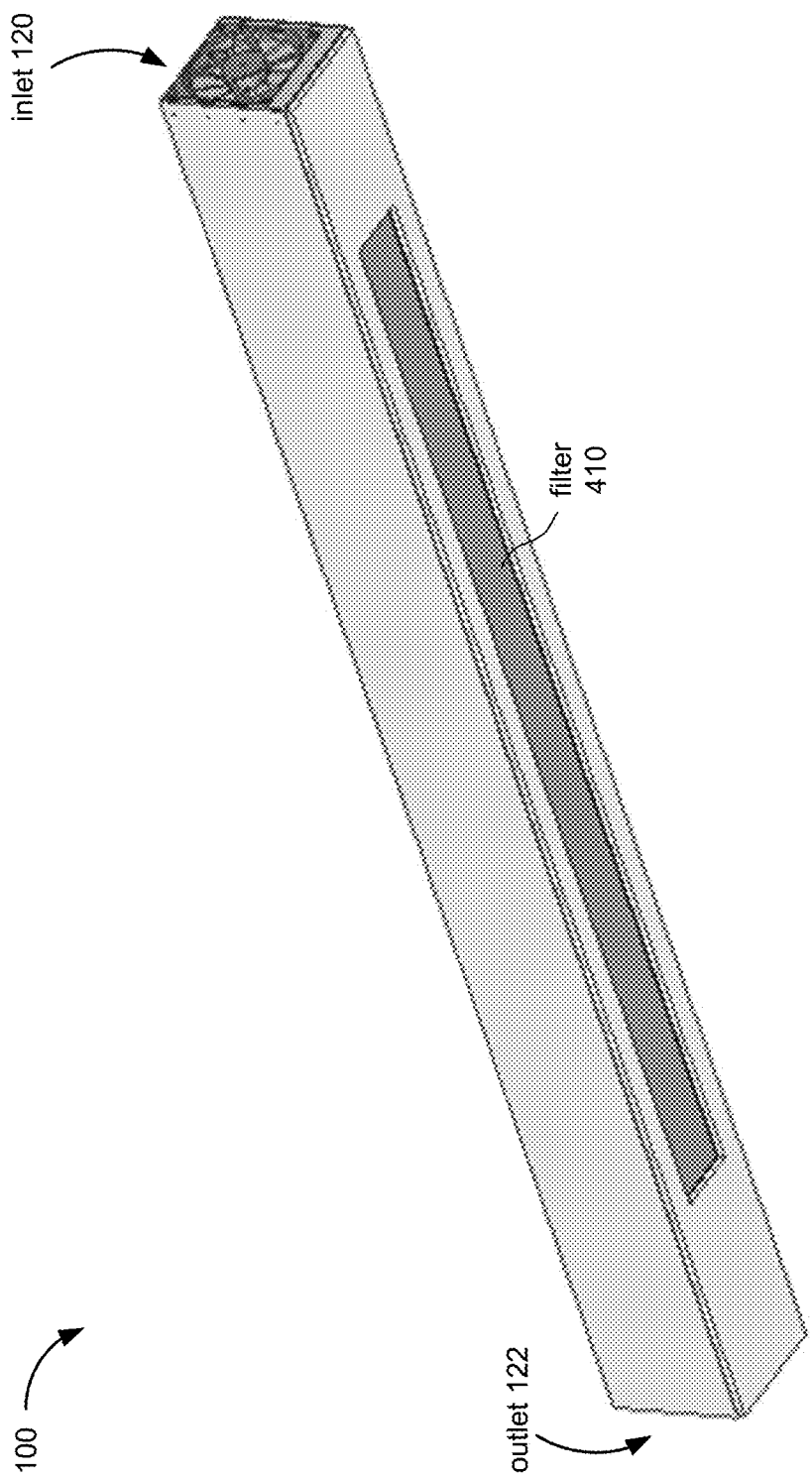
FIG. 4 illustrates an air treatment system that includes a filter in accordance with some embodiments.

FIG. 4 illustrates an air treatment system 100 that includes a filter 410 in accordance with some embodiments. In some cases, such as when air treatment system 100 is configured for use in a room that may be occupied by humans or pets, the air treatment system 100 may include a band-pass or low-pass filter 410 that is configured to block light having wavelengths near the first peak wavelength (λ1) while transmitting light having wavelengths near the second peak wavelength (λ2). For example, if the first peak wavelength (λ1) has not been approved to be safe for direct human exposure but the second peak wavelength (λ2) has been approved as being safe for direct human exposure, the band-pass or low-pass filter 410 may be configured to transmit light near the second peak wavelength (λ2) and blocking light near the first peak wavelength (λ1). Thus, air treatment system 100 may utilize the first light 139 and second light 149, having the first and second peak wavelengths, respectively, to decontaminate air that passes through the air treatment system 100 while simultaneously transmitting the second light 149 through the filter 410 without transmitting the first light 139 such that the second light 149 can be used to provide safe surface decontamination concurrently with air decontamination.

Figure 5A:
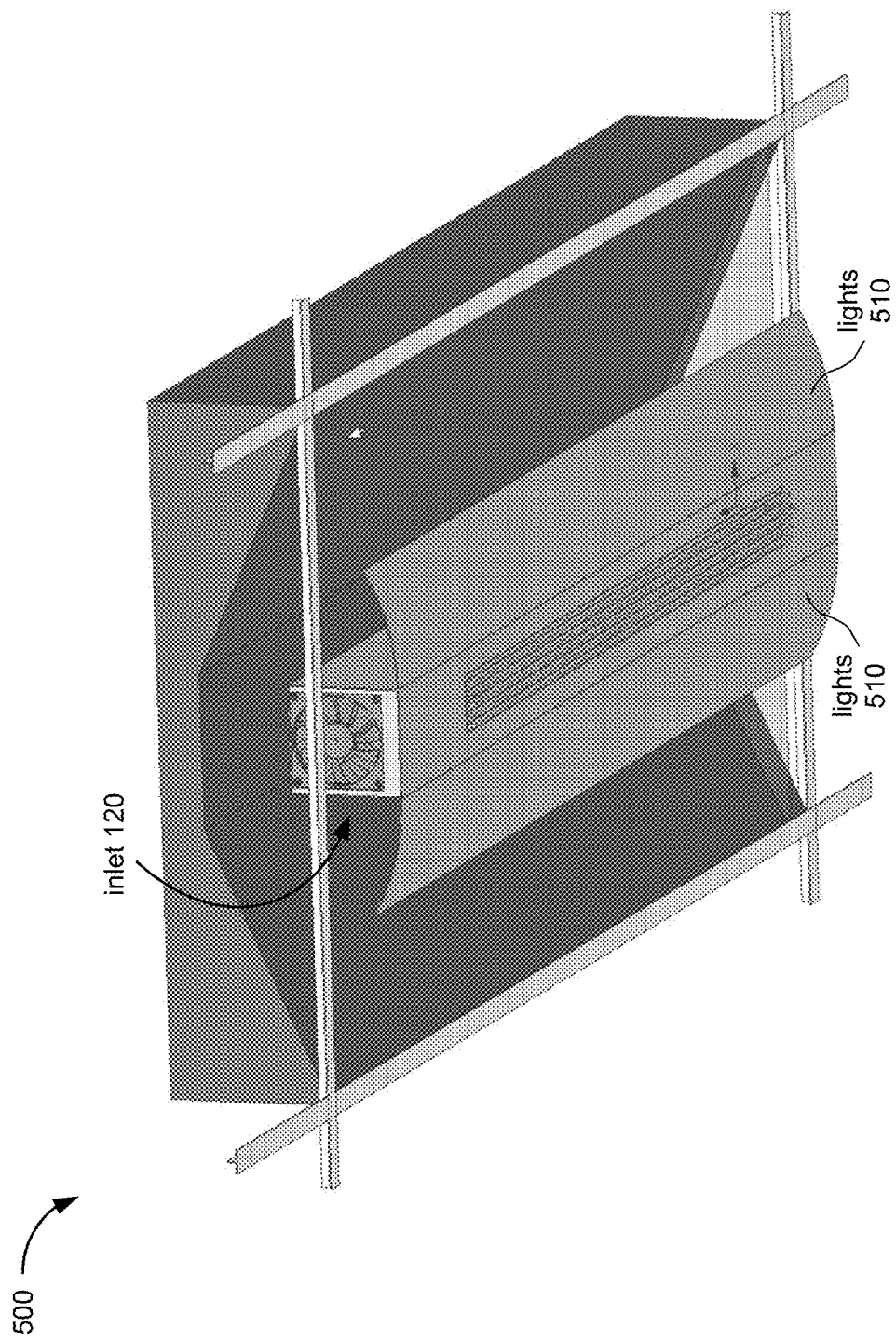
FIGS. 5A-5C illustrate air treatment systems that include an ambient UV lamp in accordance with some embodiments.
Figure 5B:
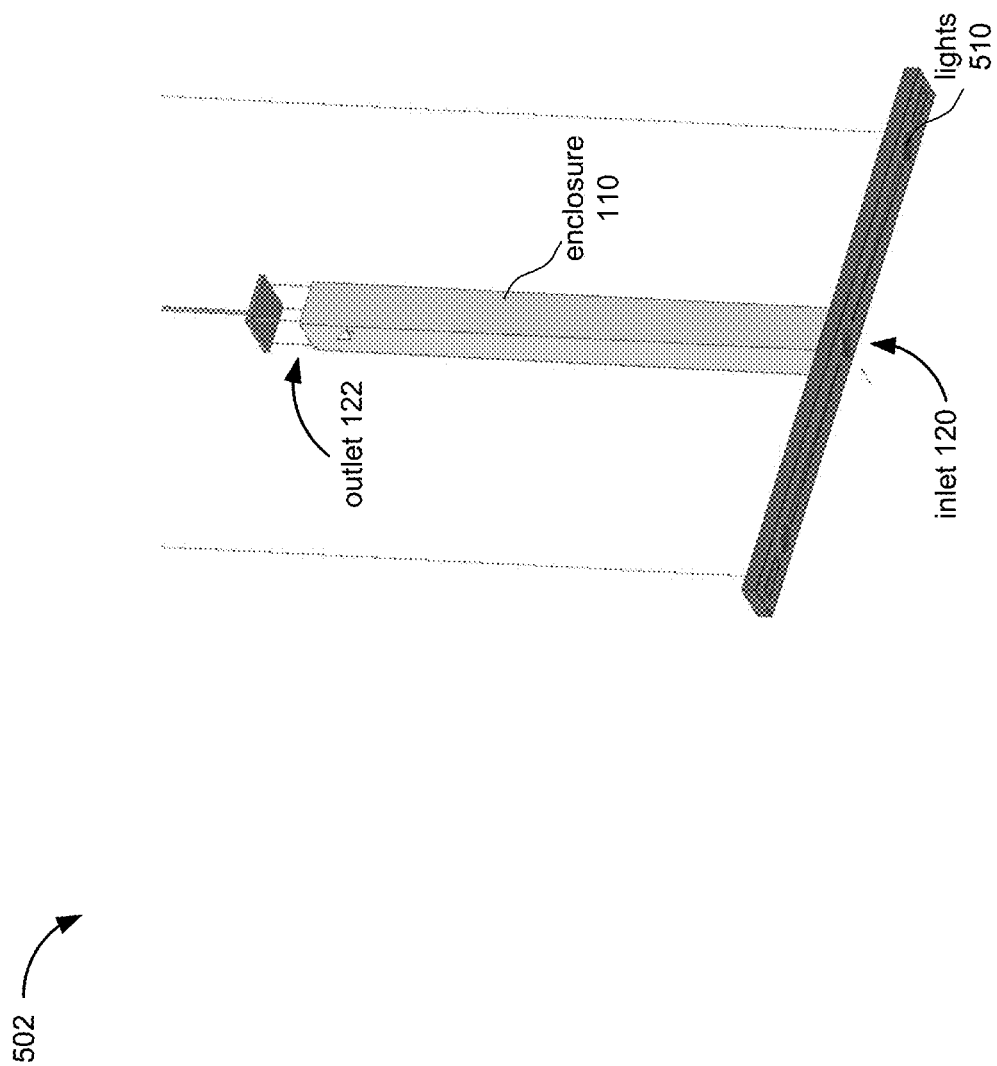
Figure 5C:

FIGS. 5A-5C illustrate air treatment systems, corresponding to air treatment system 100, that include an ambient light source in accordance with some embodiments. Descriptions provided above with respect to air treatment system 100 are not repeated for brevity.

Referring to FIG. 5A, air treatment system 500 includes one or more lights 510 that are configure to provide ambient lighting. For example, air treatment system 500 may include one or more LEDs or fluorescent light sources so that air treatment system 500 may be used to replace office lighting. For example, air treatment system 500 may have dimensions that correspond with current commercial lighting schemes, such as having an enclosure length of 4 feet, a commercial standard in many office buildings.

FIG. 5B shows an example of another air treatment system 502 that includes one or more lights 510. In this example, the enclosure 110 is vertical so that air enters the enclosure 110 from an inlet 120 that faces downward and decontaminated air is output via an outlet 122 that is disposed above the inlet 120. The one or more lights 510 are shown in a horizontal configuration to provide amply lighting in indoor spaces.

FIG. 5C shows an example of another air treatment system 502 that includes one or more lights 510 and a vertical enclosure 110. In this example, the lights 510 are disposed around the inlet 120 of the enclosure 110. For example, the lights 510 may be a ring light.

Additionally, in some implementations, as shown, the inlet 120 may also have a conical shape to facilitate the direction of air into the enclosure 110 via the inlet 120. In some implementations, the outlet 122 may also have a conical shape.

Figure 6A:
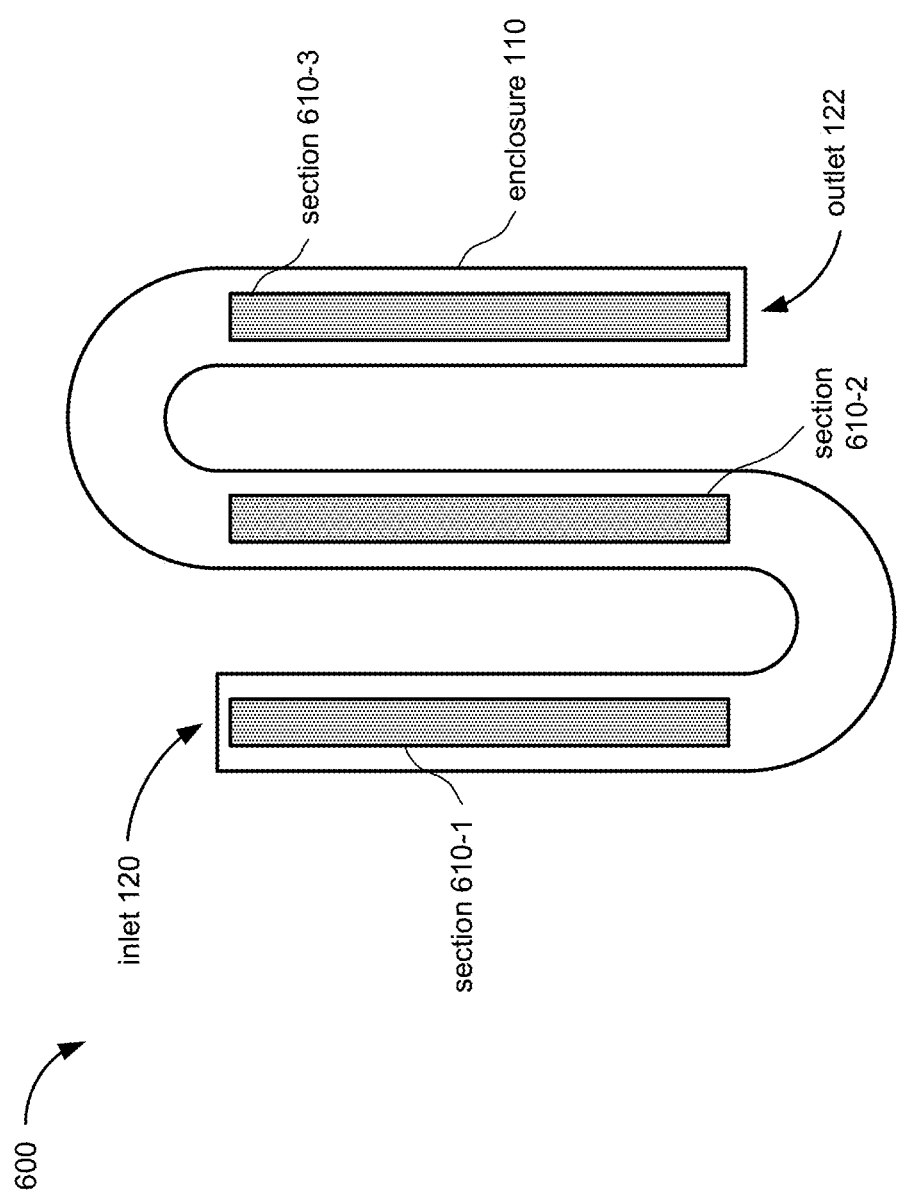
FIGS. 6A-6B illustrate different shapes of air treatment systems in accordance with some embodiments.
Figure 6B:
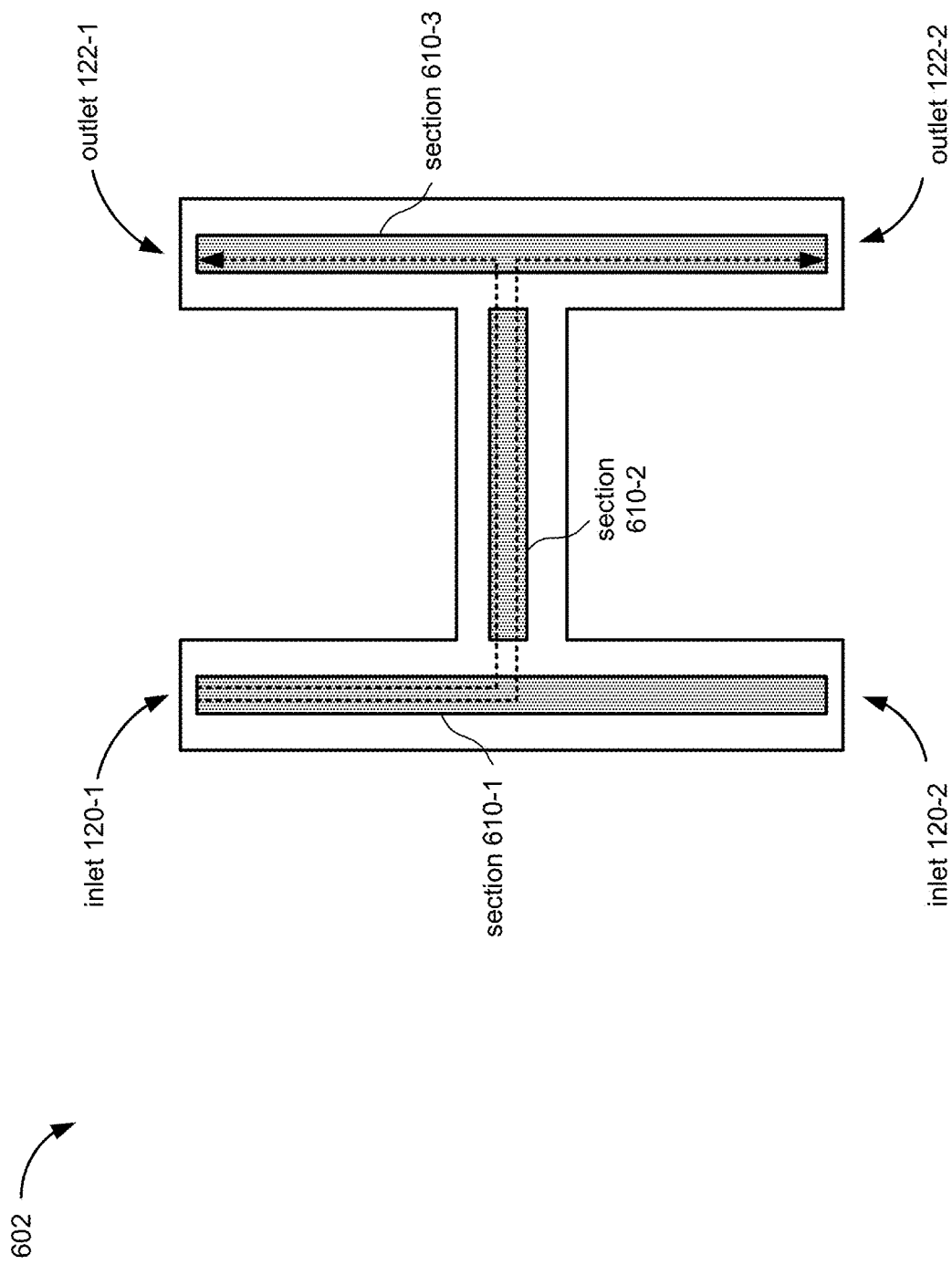

FIGS. 6A-6B illustrate different shapes of air treatment systems, corresponding to air treatment system 100, in accordance with some embodiments. FIG. 6A shows an air treatment system 600 that includes a plurality of decontamination sections 610. In this example, the enclosure 110 of the air treatment system 600 includes a passageway that has three sections 610-1, 610-2, and 610-3, represented by shaded regions. In some embodiments, each of the sections 610-1, 610-2, and 610-3 of the passageway is irradiated with both the first light and the second light. In some embodiments, one or more of the sections (e.g., section 610-2) are irradiated with at least the first light while one or more other sections (e.g., sections 610-1 and 610-3), which are closer to the inlet and the outlet, are irradiated with only the second light, which is safer for humans and animals and can escape the enclosure via the inlet and/or the outlet without endangering anyone around the air treatment system. Thus, air flowing via the passage way is irradiated with both the first light 139 and the second light 149.

FIG. 6B shows an air treatment system 602 that includes a plurality of inlets (e.g., inlets 120-1 and 120-2), a plurality of outlets (e.g., outlet 122-1 and 122-2), and a plurality of decontamination sections 610 (e.g., 610-1, 610-2, and 610-3) represented by shaded regions. In this example, the enclosure 110 of the air treatment system 600 provides multiple passageways, including, for example, a first passageway (indicated by dashed arrow) from inlet 120-1 to outlet 122-1 via a first portion (e.g. a first half) of section 610, an entirety of section 610-2, and a first portion (e.g., a first half) of section 610-3; a second passageway (indicated by another dashed arrow) from inlet 120-1 to outlet 122-2 via the first portion (e.g. the first half) of section 610, an entirety of section 610-2, and a second portion (e.g., a second half) of section 610-3; a third passageway from inlet 120-2 to outlet 122-1 via a second portion (e.g. a second half) of section 610, an entirety of section 610-2, and the first portion (e.g., the first half) of section 610-3; and a fourth passageway from inlet 120-2 to outlet 122-2 via the second portion (e.g. the second half) of section 610, an entirety of section 610-2, and the second portion (e.g., the second half) of section 610-3. In some embodiments, each of the three sections 610-1, 610-2, and 610-3 include one or more first UV lamps 130 and one or more second UV lamps such that each of the multiple passageways is irradiated with the first light 139 and the second light 149. In some embodiments, one or more of the sections (e.g., section 610-1) are irradiated with at least the first light while one or more other sections (e.g., sections 610-1 and 610-3), which are closer to the inlet and the outlet, are irradiated with only the second light, which is safer for humans and animals and can escape the enclosure via the inlet and/or the outlet without endangering anyone around the air treatment system. Thus, air flowing via each passageway is irradiated with both the first light 139 and the second light 149. Air is directed into the air treatment system 602 via any of the inlets 120-1 and 120-2 and output from the air treatment system 602 via any of the outlets 122-1 and 122-2. In some embodiments, each inlet 120 of the air treatment system 602 is spaced apart from any outlet 122 of the air treatment system 602 by a distance greater than, for example, 50 cm or 10 cm, so that the clean air released from the outlet is not drawn back into the inlet right away.

In some embodiments, the decontamination sections 610 are comparable to one another in size (e.g., dimension). In some embodiments, at least one decontamination section is different from another decontamination section in a same air treatment system. For example, a decontamination section 160-2 may have a length that is shorter or longer than a length of another decontamination section (such as section 160-1 or 160-3).

As shown in FIGS. 6A and 6B, multiple decontamination sections can be coupled together to form one or more passageways in order to achieve longer air flow duration and thus, longer air exposure time to the first light 139 and the second light 149. An air treatment system may include multiple decontamination sections arranged in various shapes or configuration (e.g., U-shape, W-shape, H-shape, spiral) so that air flowing through the air treatment system is exposed to the first light 139 and/or the second light 149 for about 0.01-2 seconds and that any pathogens in the air would receive a combined radiation dosage of about 0.05-1.2 mJ/cm$^2$ or about 0.05-0.6 mJ/cm$^2$ from the first light and the second light.

Figure 7:
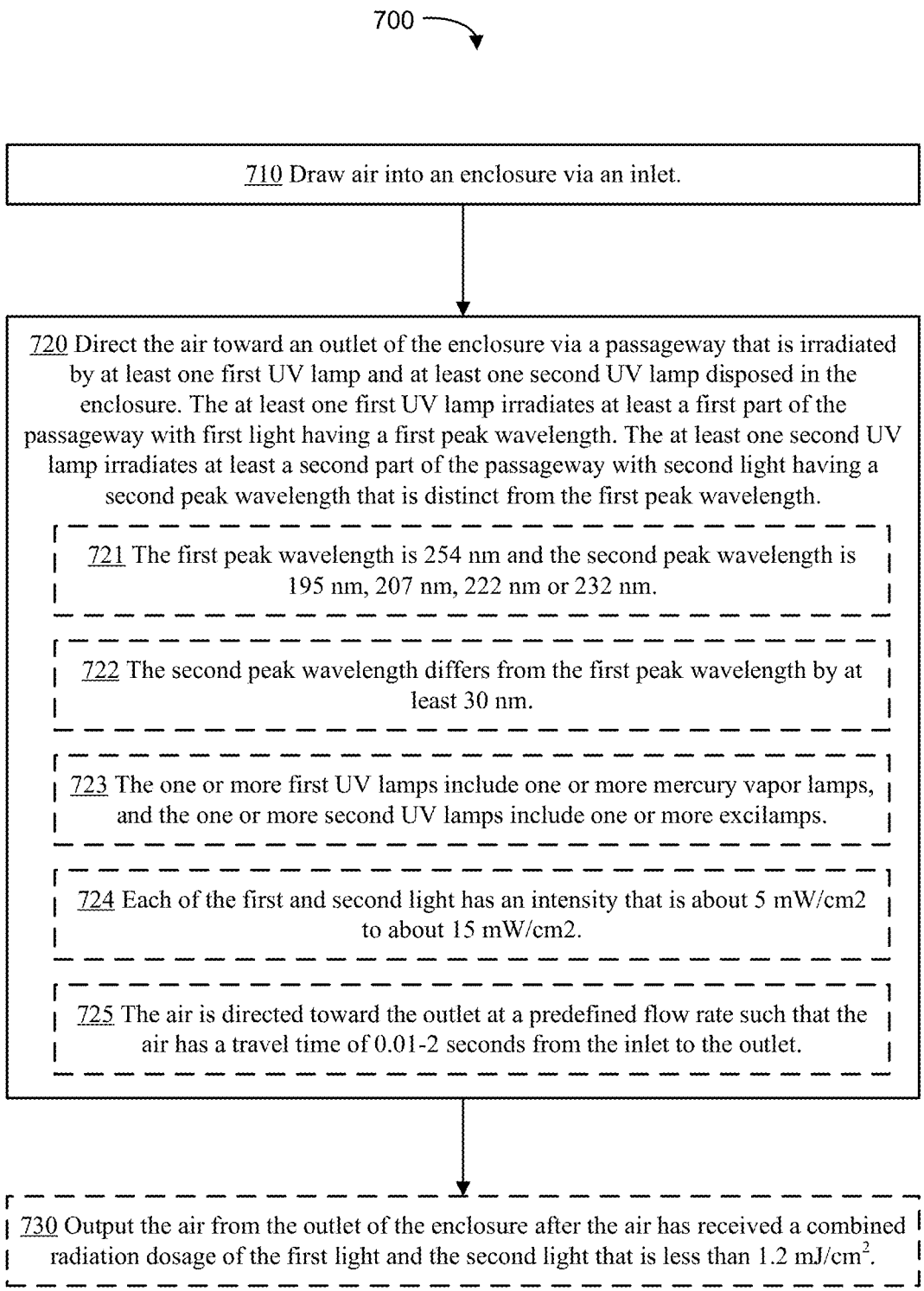
FIG. 7 illustrates a flowchart of a method of decontamination in accordance with some embodiments.

FIG. 7 illustrates a flowchart of a method 700 of treating air in accordance with some embodiments. In some embodiments, the method 700 includes drawing (710) air into an enclosure 110 via an inlet 130 and directing (720) the air toward an outlet 122 of the enclosure 110 via a passageway 124 that is irradiated by at least one first UV lamp 130 and at least one second UV lamp 140. Each of the at least one first UV lamp 130 and the at least one second UV lamp 140 is disposed inside the enclosure 110. The at least one first UV lamp 130 irradiates at least a first part of the passageway 124 with first light 139 having a first peak wavelength ($\lambda 1$). The at least one second UV lamp 140 irradiates at least a second part of the passageway 124 with second light 149 having a second peak wavelength ($\lambda 2$) that is distinct from the first peak wavelength ($\lambda 1$).

In some embodiments, (721) the first peak wavelength ($\lambda$) is 254 nm and the second peak wavelength ($\lambda 2$) is 195 nm, 207 nm, 222 nm or 232 nm In some embodiments, (722) the second peak wavelength ($\lambda 2$) differs from the first peak wavelength ($\lambda 1$) by at least 20 nm.

In some embodiments, (723) the one or more first UV lamps 130 include one or more mercury vapor lamps and/or one or more UV LED's, and the one or more second UV lamps 140 include one or more excilamps and/or one or more UV LED's.

In some embodiments, (724) the first light 139 has an intensity that is about 50 µW/cm$^2$ to about 1 mW/cm$^2$ and the second light 149 has an intensity that is about 1 mW/cm$^2$ to about 50 mW/cm$^2$ (e.g., between 5 mW/cm$^2$ to about 15 mW/cm$^2$).

In some embodiments, the air is directed (725) toward the outlet 122 at a predefined flow rate such that the air has a travel time of about 0.01 to about 2 seconds from the inlet 120 to the outlet 122.

In some embodiments, the method 700 also includes outputting (730) the air from the outlet 122 of the enclosure 110 after the air has received a combined radiation dosage of the first light 139 and the second light 149 that is in the range of 0.05-1.2 mJ/cm$^2$ or 0.05-0.6 mJ/cm$^2$.

In some embodiments, at least a portion of the first part of the passageway 124 overlaps with at least a portion of the second part of the passageway 124.

It will be understood that, although the terms first, second, etc., are, in some instances, used herein to describe various elements, these elements should not be limited by these terms. These terms are only used to distinguish one element from another. For example, a first UV lamp could be termed a second UV lamp, and, similarly, a second UV lamp could be termed a first UV lamp, without departing from the scope of the various described embodiments. The first widget and the second widget are both widget, but they are not the same condition unless explicitly stated as such.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

What is claimed is:

1. An air treatment system comprising:
an enclosure having an inlet, an outlet, and a passageway between the inlet and the outlet;
one or more air driving components configured to:
draw air into the enclosure, via the inlet; and
direct the air toward the outlet via the passageway;
one or more first UV lamps disposed in the enclosure and configured to irradiate at least a portion of the passageway with first light having a first peak wavelength at 254 nm; and
one or more second UV lamps disposed inside the enclosure and configured to irradiate the portion of the passageway with second light having a second peak wavelength at 222 nm or 232 nm, wherein the portion of the passageway is configured to be concurrently irradiated by the first light and the second light; wherein:
a first UV lamp of the one or more first UV lamps is concentrically arranged with respect to a second UV lamp of the one or more second UV lamps and with respect to a central axis of the passageway;
the passageway includes multiple interconnected chambers including a first chamber surrounded by the second UV lamp, and a second chamber surrounding the first chamber; and
the first UV lamp has a shorter length along the passageway than the second UV lamp to limit an amount of the first light from escaping the enclosure via the inlet and/or the outlet.

2. The air treatment system of claim 1, wherein:
the portion of the passageway is at least 90% of the passageway.

3. The air treatment system of claim 1, wherein:
the air directed through the passageway is output from the enclosure after receiving a combined radiation dosage of the first light and the second light that is in a range of 0.05-1.2 mJ/cm$^2$; and
each of the first light and the second light contributes 10-90% of the combined radiation dosage.

4. An air treatment system comprising:
an enclosure having an inlet, an outlet, and a passageway between the inlet and the outlet;
one or more air driving components configured to:
draw air into the enclosure, via the inlet; and
direct the air toward the outlet via the passageway;
one or more first UV lamps disposed in the enclosure and configured to irradiate at least a portion of the passageway with first light having a first peak wavelength at 254 nm; and
one or more second UV lamps disposed inside the enclosure and configured to irradiate the portion of the passageway with second light having a second peak wavelength at 222 nm or 232 nm, wherein the portion of the passageway is configured to be concurrently irradiated by the first light and the second light; wherein:
the enclosure includes multiple sections including a first section near the inlet, a second section near the outlet, and a third section between the first section and the second section;
the one or more first UV lamps is disposed in the third section; and
the one or more second UV lamps includes at least one second UV lamp disposed in the first section and at least one second UV lamp disposed in the second section.

5. The air treatment system of claim 1, wherein:
the one or more first UV lamps include one or more UV lamps selected from the group consisting of mercury vapor lamps and UV LEDs; and
the one or more second UV lamps include one or more UV lamps selected from the group consisting of excilamps and UV LEDs.

6. The air treatment system of claim 1, wherein:
the passageway has a length equal to about 400 mm to 2000 mm; and
each of the first UV lamp and the second UV lamp extends along more than half of the length of the passageway.

7. The air treatment system of claim 1, wherein the one or more air driving components are configured to direct the air toward the outlet via the passageway such that the air has a travel time of 0.01-2 seconds from the inlet to the outlet.

8. The air treatment system of claim 1, wherein the first light has an intensity that is about 50 µW/cm$^2$ to about 1 mW/cm$^2$ and the second light has an intensity that is about 1 mW/cm$^2$ to about 50 mW/cm$^2$.

9. The air treatment system of claim 1, wherein of a combined intensity of the first and second light is about 1 mW/cm$^2$ to about 30 mW/cm$^2$.

10. The air treatment system of claim 1, wherein:
the first UV lamp of the one or more first UV lamps is disposed in the first chamber and the second UV lamp of the one or more second UV lamps surrounds the first UV lamp.

11. A method of treating air, comprising:
drawing air into an enclosure via an inlet; and
directing the air toward an outlet of the enclosure via a passageway that is irradiated by one or more first UV lamps and one or more second UV lamps disposed in the enclosure, wherein:
the one or more first UV lamps irradiating at least a portion of the passageway with first light having a first peak wavelength at 254 nm; and
the one or more second UV lamps irradiating the portion of the passageway with second light having a second peak wavelength that is at 222 nm or 232 nm;
the method further comprising:
directing the air through multiple interconnected chambers including flowing a first portion and a second portion of the air concurrently and respectively through a first chamber and a second chamber, the first chamber being surrounded by one of the one or more second UV lamps and the second chamber surrounding the first chamber, wherein the one or more first UV lamp includes a first UV lamp surrounded by the first chamber; and
the first UV lamp has a shorter length along the passageway than one of the one or more second UV lamps to limit an amount of the first light from escaping the enclosure via the inlet and/or the outlet.

12. The method of claim 11, further comprising:
outputting the air from the outlet of the enclosure after the air has received a combined radiation dosage of the first light and the second light that is in a range of 0.05-1.2 mJ/cm$^2$; and
wherein each of the first light or the second light contributes 10-90% of the combined radiation dosage.

13. The method of claim 11, wherein:
the one or more first UV lamps include one or more UV lamps selected from the group consisting of mercury vapor lamps and UV LEDs; and
the one or more second UV lamps include one or more UV lamps selected from the group consisting of excilamps and UV LEDs.

14. The method of claim 11, wherein a combined intensity of the first and second light is about 1 mW/cm$^2$ to about 30 mW/cm$^2$.

15. The method of claim 11, wherein:
the air is directed toward the outlet at a predefined flow rate such that the air has a travel time of 0.01-2 seconds from the inlet to the outlet.

16. The air treatment system of claim 4, wherein:
the first and second sections are configured to be irradiated with only the second light; and
the third section is configured to be irradiated with the first light and the second light.

17. The air treatment system of claim 4, wherein the one or more air driving components are configured to direct the air toward the outlet via the passageway such that the air has a travel time of 0.01-2 seconds from the inlet to the outlet.

18. The air treatment system of claim 4, wherein the first light has an intensity that is about 50 µW/cm$^2$ to about 1 mW/cm$^2$ and the second light has an intensity that is about 1 mW/cm$^2$ to about 50 mW/cm$^2$.

19. The air treatment system of claim 4, wherein the portion of the passageway is between the first section and the second section, and wherein a combined intensity of the first and second light in the portion of the passageway is about 1 mW/cm$^2$ to about 30 mW/cm$^2$.

* * * * *